US012680643B2

(12) United States Patent　　　(10) Patent No.:　　US 12,680,643 B2

Casura et al.　　　　　　　　　　(45) Date of Patent:　　*Jul. 14, 2026

(54) ASEPTIC FLUID COUPLINGS

(71) Applicant: Colder Products Company, Roseville, MN (US)

(72) Inventors: Matthew G. Casura, St. Anthony, MN (US); Loi T. Truong, Savage, MN (US)

(73) Assignee: Colder Products Company, Roseville, MN (US)

( * ) Notice: Subject to any disclaimer, the term of this patent is extended or adjusted under 35 U.S.C. 154(b) by 22 days.

This patent is subject to a terminal disclaimer.

(21) Appl. No.: 18/937,407

(22) Filed: Nov. 5, 2024

(65) Prior Publication Data

US 2025/0116363 A1　　Apr. 10, 2025

Related U.S. Application Data

(63) Continuation of application No. 18/220,528, filed on Jul. 11, 2023, now Pat. No. 12,140,256, which is a continuation of application No. 17/838,357, filed on Jun. 13, 2022, now Pat. No. 11,739,872.

(60) Provisional application No. 63/211,724, filed on Jun. 17, 2021.

(51) Int. Cl.
　　*F16L 37/35*　　　　(2006.01)
　　*A61M 39/18*　　　　(2006.01)
　　*A61M 39/26*　　　　(2006.01)

(52) U.S. Cl.
　　CPC .............. *F16L 37/35* (2013.01); *A61M 39/18* (2013.01); *A61M 39/26* (2013.01); *A61M 2205/273* (2013.01); *F16L 2201/44* (2013.01)

(58) Field of Classification Search
　　CPC ....... F16L 37/35; F16L 37/34; F16L 2201/44; A61M 39/18; A61M 39/26; A61M 2039/267; A61M 2205/273
　　See application file for complete search history.

(56) References Cited

U.S. PATENT DOCUMENTS

| | | | |
|---|---|---|---|
| 4,334,551 A | | 6/1982 | Pfister |
| 4,429,713 A | * | 2/1984 | Walter .................... F16L 37/34 |
| | | | 251/149.8 |
| 4,664,148 A | | 5/1987 | Magnuson |

(Continued)

FOREIGN PATENT DOCUMENTS

| | | |
|---|---|---|
| EP | 0028601 | 5/1981 |
| GB | 2269224 | 2/1994 |

(Continued)

OTHER PUBLICATIONS

Extended European Search Report in European Appln No. 22825585, dated Sep. 3, 2024, 9 pages.

(Continued)

*Primary Examiner* — David Colon-Morales

(74) *Attorney, Agent, or Firm* — Fish & Richardson P.C.

(57)　　　　　　ABSTRACT

Some fluid coupling devices described herein are configured for use in fluid systems for purposes of providing a single-use, aseptic disconnection functionality that substantially prevents fluid spillage when being disconnected. In some embodiments, the coupling portions cannot be functionally reconnected to each other after being disconnected from each other.

20 Claims, 19 Drawing Sheets

(56)                References Cited

U.S. PATENT DOCUMENTS

| | | | | |
|---|---|---|---|---|
| 4,804,015 | A | 2/1989 | Albinsson | |
| 5,106,127 | A | 4/1992 | Briet | |
| 5,806,564 | A | 9/1998 | Wilcox | |
| 5,971,019 | A | 10/1999 | Imal | |
| 6,024,124 | A | 2/2000 | Braun et al. | |
| 6,161,578 | A * | 12/2000 | Braun | F16L 37/35 |
| | | | | 137/614.04 |
| 6,237,631 | B1 | 5/2001 | Giesler et al. | |
| 6,302,147 | B1 | 10/2001 | Rose et al. | |
| 7,350,535 | B2 * | 4/2008 | Liepold | F16K 15/18 |
| | | | | 137/553 |
| 7,469,472 | B2 | 12/2008 | deCler et al. | |
| 7,547,047 | B2 | 6/2009 | deCler et al. | |
| 7,631,660 | B2 * | 12/2009 | deCler | F16L 37/098 |
| | | | | 137/614.05 |
| 7,959,192 | B2 | 6/2011 | Elton et al. | |
| 8,671,964 | B2 * | 3/2014 | Py | F16L 41/02 |
| | | | | 137/614.04 |
| 8,690,120 | B2 | 4/2014 | Hartnett et al. | |
| 9,901,729 | B2 * | 2/2018 | Vigna | A61M 39/18 |
| 10,022,532 | B2 * | 7/2018 | Burdge | F16L 37/35 |
| 11,480,281 | B2 * | 10/2022 | Benson | A61M 39/1011 |
| 11,566,736 | B2 * | 1/2023 | Truong | F16L 37/248 |
| 11,614,192 | B2 * | 3/2023 | Benson | F16L 37/30 |
| | | | | 251/148 |
| 11,635,162 | B2 * | 4/2023 | Martin | F16L 37/0841 |
| | | | | 285/317 |
| 11,739,872 | B2 * | 8/2023 | Casura | A61M 39/1011 |
| | | | | 251/149.1 |
| 12,140,256 | B2 * | 11/2024 | Casura | A61M 39/165 |
| 2005/0076964 | A1 | 4/2005 | Whall | |
| 2007/0025811 | A1 | 2/2007 | Wilhelm | |
| 2007/0073215 | A1 | 3/2007 | Wieslander | |
| 2008/0185056 | A1 | 8/2008 | Diodati et al. | |
| 2009/0051161 | A1 | 2/2009 | Eskstrom | |
| 2009/0076434 | A1 | 3/2009 | Mischelevich | |
| 2010/0183361 | A1 | 7/2010 | Davis | |
| 2010/0230950 | A1 | 9/2010 | Scott et al. | |
| 2011/0240158 | A1 | 10/2011 | Py | |
| 2012/0031515 | A1 | 2/2012 | Whitaker | |
| 2013/0341904 | A1 | 12/2013 | Lehmann et al. | |
| 2014/0345748 | A1 * | 11/2014 | Rogers | A61J 1/12 |
| | | | | 141/330 |
| 2015/0028586 | A1 * | 1/2015 | Gerst | A61M 39/1011 |
| | | | | 285/352 |
| 2016/0158519 | A1 | 6/2016 | Rhinehart | |
| 2017/0202741 | A1 * | 7/2017 | Py | A61M 39/18 |
| 2018/0296817 | A1 * | 10/2018 | Burdge | A61M 39/26 |
| 2019/0298985 | A1 | 10/2019 | Truong | |
| 2021/0199220 | A1 | 7/2021 | Truong | |
| 2021/0388930 | A1 | 12/2021 | Benson | |

FOREIGN PATENT DOCUMENTS

| | | |
|---|---|---|
| WO | WO 1980/001507 | 7/1980 |
| WO | WO 2008/094707 | 8/2008 |
| WO | WO 2012/114105 | 8/2012 |
| WO | WO 2014/160756 | 10/2014 |
| WO | WO 2016/172229 | 10/2016 |
| WO | WO 2017/062859 | 4/2017 |

OTHER PUBLICATIONS

International Search Report and Written Opinion in International
Appln. No. PCT/US2022/033182, mailed on Sep. 8, 2022, 9 pages.

* cited by examiner

220'

220'

222a'

224'

222b'

220'

224'

ASEPTIC FLUID COUPLINGS

CROSS-REFERENCE TO RELATED APPLICATIONS

This application is a continuation application of U.S. patent application Ser. No. 18/220,528 filed Jul. 11, 2023, now U.S. Pat. No. 12,140,256, which is a continuation application of U.S. patent application Ser. No. 17/838,357 filed Jun. 13, 2022, now U.S. Pat. No. 11,739,872, which claims the benefit of U.S. Provisional Application Ser. No. 63/211,724 filed Jun. 17, 2021. The disclosure of the prior applications are considered part of (and are incorporated by reference in) the disclosure of this application.

BACKGROUND

1. Technical Field

This document relates to fluid coupling devices for fluid systems and methods. For example, some embodiments described in this document relate to single-use, aseptic disconnection fluid coupling devices.

2. Background Information

Fluid systems commonly include components such as tubing, pumps, reservoirs, fittings, couplings, heat exchangers, sensors, filters, valves, seals, and the like. Such components can be connected together in a network to define one or more fluid flow paths. Some fluid systems are open systems, meaning that the fluid flows through the network once and then exits the network or is open to the environment. Other fluid systems are closed systems, meaning that the fluid recirculates within the network of components.

Fluids may be moved through fluid systems using fluid pressure differentials. For example, in some cases, a pump or a vacuum source is used to create a pressure differential that causes the fluid to flow within the fluid system. In another example, gravity is used to cause the fluid to flow within the fluid system. In still other examples, mechanical means can be used to exert exterior force on a tube or reservoir causing fluid to flow. A peristaltic pump is one example. In other examples, a combination of such techniques is used to cause the fluid to flow within the fluid system.

Some fluid couplings can be used for sterile fluid conveyance, such as for connecting a source of one or more sterile ingredients to a sterile processing system, such as a bioreactor or other type of sterile system or container. Fluid couplings for sterile fluid conveyance can also be used for extracting samples from a sterile processing system. Fluid couplings for sterile fluid conveyance can also be used to connect together two or more pieces of sterile processing equipment.

In the context of some fluid systems, such as some bioprocessing fluid systems, it may be desirable to have a tube coupler that can aseptically disconnect a fluid flow path. In one such example implementation, it is desirable to disconnect aseptically one or more containers (e.g., media bags) from a bioreactor system. In that scenario, an aseptic coupling can be used to disconnect the container(s) from the bioreactor system while substantially preventing biological contamination of the containers, of tubing, of other connected components, and of the bioreactor via the disconnected ends of the coupling during and after the disconnection process. Such an aseptic coupling will also serve to limit the exposure of the fluid to the surrounding environment.

SUMMARY

This document describes fluid coupling devices for fluid systems and methods. In some embodiments, the fluid coupling devices can be implemented as single-use, aseptic disconnection fluid coupling devices that are configured to reduce the likelihood of fluid spillage when being disconnected. In some embodiments, the coupling portions cannot be reconnected to each other (or to other couplings) after being disconnected from each other. Accordingly, the fluid coupling devices are called "single-use" disconnect couplings. In the context of this disclosure, the term "fluid" means any substance that can be made to flow including, but is not limited to, liquids, gases, granular or powdered solids, mixtures or emulsions of two or more fluids, suspensions of solids within liquids or gases, vapors, steam, mists, gels, semi-solids, etc.

In particular embodiments, the fluid coupling devices described herein are single-use devices because, after the two portions of the coupling (also referred to herein as "coupling halves" and/or "connectors") are disconnected from each other, the fluid paths of one or both portions are irreversibly blocked. Hence, in these particular embodiments, the fluid coupling devices provided herein are structurally configured to be single-use disconnection devices so that, after the single-use coupling halves have been disconnected from each other, they cannot be operably reconnected to each other (or to any other coupling halves) so as to reestablish an open fluid flow path therethrough, and/or cannot be mechanically reconnected to each other.

Additionally, in such single-use embodiments or in other embodiments, the fluid coupling devices can be configured as "aseptic" coupling devices in that, during disconnection and after the two portions of the coupling device are disconnected from each other, the fluid paths of both portions are mechanically blocked, e.g., by a valve, so as to inhibit biological contamination migrating into the flow paths. Such an "aseptic" coupling will also serve to limit the exposure of the fluid to the surrounding environment. As used herein, the term "aseptic" refers to any process or device that maintains a sterilized surface or volume. "Sterile" as used herein refers to being free from bacteria or other living microorganisms, or being/having below a particular level of bacteria or other living microorganisms.

Further, in such single-use embodiments, or other embodiments, the fluid coupling devices can be configured as no-spill coupling devices because, as the two portions of the coupling device are being disconnected from each other, one or more mechanical components will reduce the likelihood of fluid discharge out of the fluid system (for example, by blocking as such discharge paths), and/or by preventing spillage by limiting fluid inclusion incurred when couplings are connected to each other.

In one aspect, this disclosure is directed to a fluid coupling device. For example, this disclosure is directed to a single-use aseptic fluid coupling assembly. In some embodiments, such a single-use aseptic fluid coupling assembly defines a longitudinal axis and an open fluid flow path through the fluid coupling assembly along the longitudinal axis. The fluid coupling assembly can include: (i) a first coupling connected to (ii) a second coupling, and (iii) a removable sleeve surrounding portions of the first and second couplings. The first coupling can include a first housing, a first member fixedly coupled to the first housing and including a first termination, a first valve fixedly coupled to the first member, and a first sleeve disposed between the first housing and the first valve. The first sleeve can be translatable along the longitudinal axis. The second coupling can include a second collar, a second member fixedly coupled to the second collar and including a second termination, and a second valve that can be translatable along the longitudinal axis. The first valve is releasably latched to the second valve.

Such a fluid coupling assembly can optionally include one or more of the following features. The first coupling may also include a spring disposed between the first housing and the first sleeve. In some embodiments, the spring is not in the open fluid flow path. The first sleeve may be removably coupled to the second collar. The first housing may be spaced apart from the second collar. The first sleeve may include one or more projections that are movably disposed in one or more slots defined by the second collar. The one or more slots may each include: (i) a circumferentially extending portion, (ii) a portion that extends along an acute angle relative to the longitudinal axis, and/or (iii) a longitudinally extending portion that has an open end. In some embodiments, each projection of the one or more projections is movably disposed in the circumferentially extending portion of a slot of the one or more slots. The fluid coupling assembly may also include a coupling seal attached to the second member. The first sleeve may be sealed against the coupling seal. The coupling seal may include an annular seal portion and a face seal portion. The first sleeve may be sealed against the annular seal portion and the face seal portion.

In another aspect, this disclosure is directed to a single-use aseptic fluid coupling assembly that includes: (i) a first coupling connected to (ii) a second coupling, and (iii) a removable sleeve surrounding portions of the first and second couplings. The fluid coupling assembly defines a longitudinal axis and an open fluid flow path through the fluid coupling assembly along the longitudinal axis. The first coupling and second coupling are configured to be disconnected from each other by performing steps a-d in sequential order: (a) uncoupling the removable sleeve from the first and second couplings; (b) rotating a housing of the first coupling in a first direction about the longitudinal axis; (c) translating the housing of the first coupling along the longitudinal axis toward the second coupling; and (d) rotating the first coupling relative to the second coupling in a second direction about the longitudinal axis. The first direction is opposite of the second direction.

Such a single-use aseptic fluid coupling assembly may optionally include one or more of the following features. In some embodiments, during the step (b) the housing is rotated about a sleeve of the first coupling. In particular embodiments, during the step (c) the housing is translated along the sleeve. A first valve of the first coupling may be releasably latched to a second valve of the second coupling. The first and second valves may become unlatched from each other during the step (d). A first valve of the first coupling and a second valve of the second coupling may each move during the step (c) and close the open fluid flow path at the completion of the step (c). In some embodiments, the steps (b)-(d) cannot be performed until after completion of the step (a). In particular embodiments, the steps (c) and (d) cannot be performed until after completion of the step (b). In certain embodiments, the step (d) cannot be performed until after completion of the step (c). In example embodiments, the first coupling cannot be disconnected from the second coupling until after completion of the step (d).

Particular embodiments of the subject matter described in this document can be implemented to realize one or more of the following advantages. First, the coupling halves of the fluid coupling devices provided herein are designed so that the uncoupling process involves closing valves in a particular sequence so that spillage (discharge) of fluid is eliminated or minimized (i.e., a non-spill disconnection capability).

Second, in some embodiments, the fluid coupling devices are designed to be used with tubing that is relatively large (e.g., diameters of ¼ inch and larger), and to provide flow characteristics consistent with such large diameter tubing.

Third, some embodiments of the fluid coupling devices provide an improved aseptic disconnection capability that may optionally reduce or eliminate the need for sterile rooms or sterile benchtop environments in some cases. As such, these embodiments of the aseptic fluid coupling devices described herein may facilitate efficient and cost-effective operations or uses that would otherwise be high-cost or even cost prohibitive in some traditional settings that required the disconnection of particular fluid couplings in a sterile room or within a sterile flow-hood to prevent biological contamination.

Fourth, some embodiments of the fluid coupling devices provided herein are advantageously designed to be single use couplings that cannot be operatively reconnected to reestablish an open flow path therethrough. Accordingly, the potential for contamination from reuse is prevented.

Fifth, some embodiments of the fluid coupling devices provided herein include a fluid flow path that is a metallic-free.

Unless otherwise defined, all technical and scientific terms used herein have the same meaning as commonly understood by one of ordinary skill in the art to which this disclosure pertains. In addition, the materials, methods, and examples of the embodiments described herein are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION OF ILLUSTRATIVE EMBODIMENTS

Figure 1:
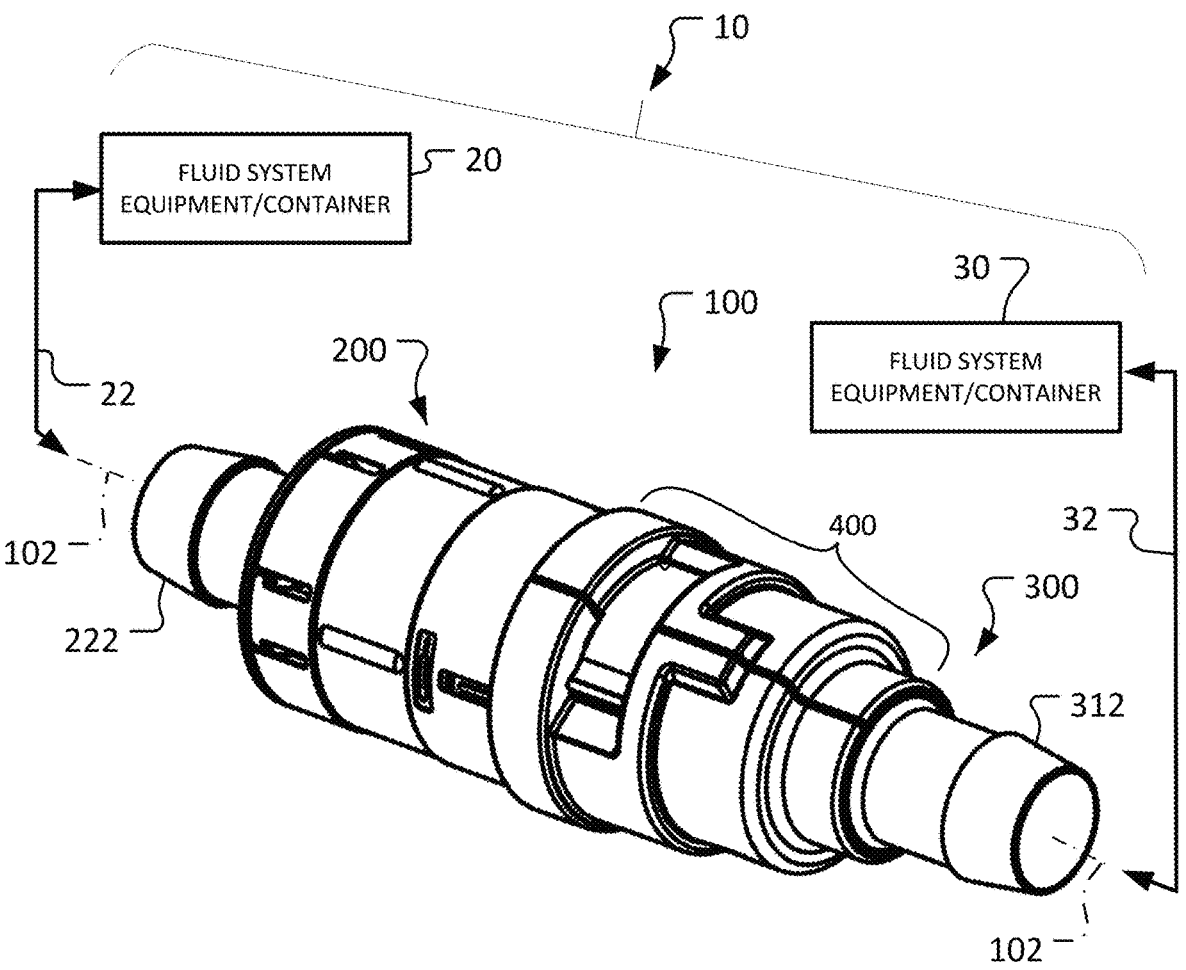
FIG. 1 is a perspective view of an example fluid system including an example fluid coupling assembly arranged in an operative connected configuration, in accordance with some embodiments provided herein.
Figure 2:
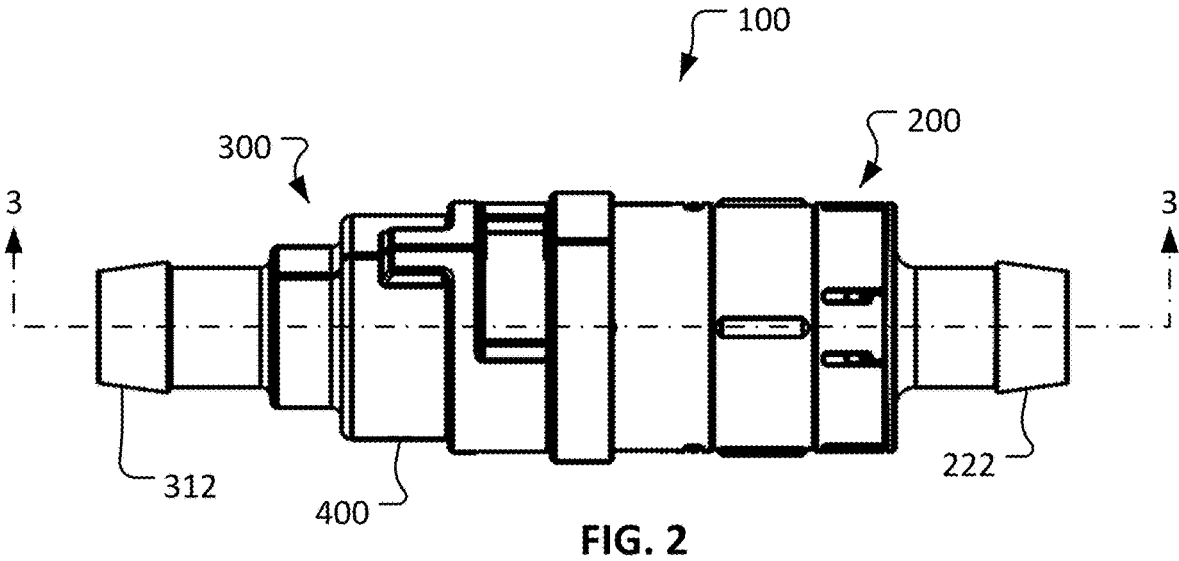
FIG. 2 is a side view of the fluid coupling assembly of FIG. 1 arranged in the operative connected configuration.
Figure 3:
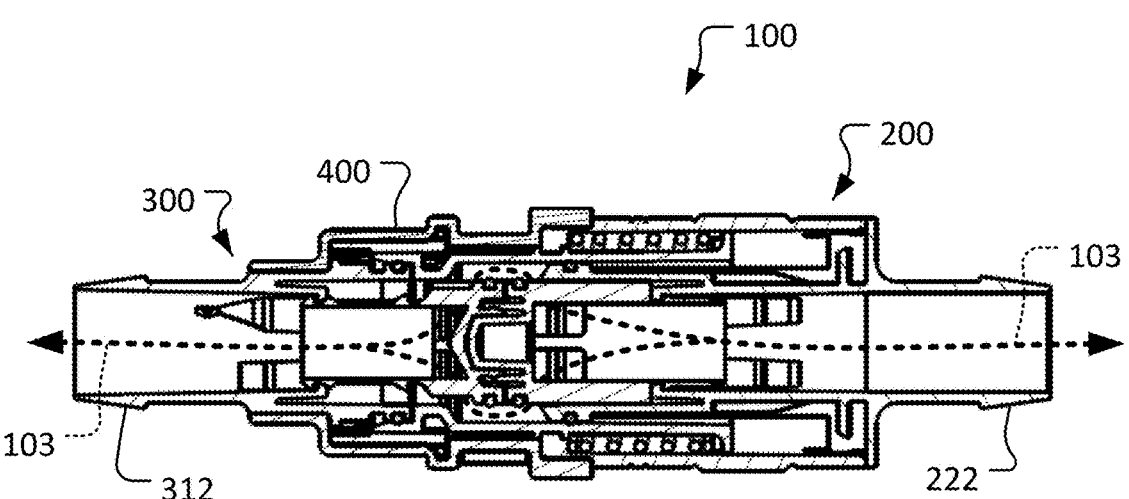
FIG. 3 is a longitudinal cross-sectional view of the fluid coupling assembly of FIG. 2 taken along the break line 3-3.

Referring to FIGS. 1-3, some example embodiments of a fluid system 10 include one or more example fluid coupling assembly 100 configured to, for example, releasably connect a first fluid system equipment or container 20 to a second fluid system equipment or container 30. In some implementations, the fluid system 10 may include at least one fluid coupling assembly 100 that is a single-use, aseptic disconnection fluid coupling device. The fluid coupling assembly 100 (or more simply, the "fluid coupling 100") defines a longitudinal axis 102 (FIG. 1), and an open fluid flow path 103 (FIG. 3) exists through the fluid coupling device 100 along the longitudinal axis 102. The depicted configuration of the fluid coupling assembly 100 in which the open fluid flow path 103 exists is also referred to herein as the "operable configuration."

In one non-limiting example, the fluid coupling 100 can provide a single-use, aseptic disconnection capability for a fluid path between the fluid system equipment 20 in the form of a bioreactor system (connected directly to the coupling device 100 or connected via a fluid tube 22) and the fluid system container 30 in the form of a media bag (connected directly to the coupling device 100 or connected via a fluid tube 32).

In the depicted embodiment, the fluid coupling assembly 100 includes a first coupling 200, a second coupling 300, and a removable sleeve 400. After the fluid transfer functionality of the fluid coupling assembly 100 has been used, the fluid coupling assembly 100 can be disconnected. That is, a user can disconnect the fluid coupling assembly 100 by removing the removable sleeve 400 and then separating the first coupling 200 and the second coupling 300 (e.g., see FIGS. 5, 8, and 9. This disconnection process is described in further detail below.

The first coupling 200 and the second coupling 300 are configured to disconnect from one another in a manner that provides an aseptic disconnection, and that mechanically prevents reconnection and reuse of the fluid flow path 103 through the first coupling 200 and the second coupling 300. As used herein, the term "aseptic" refers to any process that maintains a sterilized surface or volume. The first coupling 200 and the second coupling 300 are sometimes referred to herein as "coupling halves" or a "coupling-half" even though the first coupling 200 and the second coupling 300 are not necessarily equal halves in terms of size, shape, weight, features, or functionality.

In some cases, the fluid coupling assembly 100 is provided to the end user in a sterile condition, or is made to be compatible with sterilization. As used herein, the term "sterilize" means a process of freeing, to a specified degree, a surface or volume from microorganisms. In example embodiments, the sterility of various components can be achieved using one or more sterilization techniques, including gamma irradiation, E-beam, ethylene oxide (EtO), and/or autoclave technologies. In some cases, the fluid coupling device 100 is provided to the end user as a component of a system.

Generally, the fluid coupling assembly 100 is provided to an end user in the coupled arrangement, and with removable sleeve 400 surrounding the coupled mating coupling halves 200 and 300, as depicted in FIGS. 1-3. The end user will use the fluid coupling assembly 100 in the coupled arrangement, and then after such use will disconnect the first coupling 200 and the second coupling 300. When the disconnection is performed, the fluid flow paths 103 in each of the coupling halves 200 and 300 are aseptically sealed in a closed state. In addition, as the disconnection of the coupling halves 200 and 300 is performed, no fluid (or only a minimal amount of fluid) is spilled during the disconnection process.

The first coupling 200 includes a first termination 222. The second coupling 300 includes a second termination 312. While the first and second terminations 222 and 312 are depicted as barbed connections, it should be understood that the coupling halves 200 and 300 can have any type of connections such as, but not limited to, threaded connections, elbows, tees, sanitary fittings, compression fittings, and the like, and combinations thereof.

The materials from which one or more of the components of the fluid coupling assembly 100 are made of include thermoplastics or thermosets. In particular embodiments, the materials from which the components of the fluid coupling assembly 100 are made of are thermoplastics, such as, but not limited to, acetal, ABS, polycarbonate, polysulfone, polyether ether ketone, polysulphide, polyester, polyvinylidene fluoride (PVDF), polyethylene, polyphenylsulfone (PPSU; e.g., Radel®), polyetherimide (PEI; e.g., Ultem®), polypropylene, polyphenylene, polyaryletherketone, and the like, and combinations thereof. In some embodiments, the thermoplastics can include one or more fillers such as, but not limited to, glass fiber, glass bead, carbon fiber, talc, etc.

In some embodiments, the materials from which one or more of the components of the fluid coupling assembly 100 are made of include metals such as, but not limited to stainless steel, brass, aluminum, plated steel, zinc, and the like. In particular embodiments, one or both of the coupling halves 200 and 300 is/are metallic-free.

In some embodiments, one or both of the coupling halves 200 and/or 300 includes one or more plastic or metallic spring members (e.g., spring steel, stainless steel such as 316L, piano/music wire, beryllium copper, titanium, Hastelloy®, Inconel®, and the like).

In certain embodiments, fluid coupling assembly 100 includes one or more gaskets or seals that are made of materials such as, but not limited to, silicone, fluoroelastomers (FKM), ethylene propylene diene monomer (EPDM), thermoplastic elastomers (TPE), buna, buna-N, thermoplastic vulcanizates (TPV), and the like. In some embodiments, the gaskets or seals can have a cross-sectional shape that is an hourglass-shape, an oval shape, a circular shape, D-shaped, X-shaped, square, rectangular, U-shaped, a polygonal shape, a multi-lobe shape, or any other suitable shape, without limitation.

FIGS. 4-8 illustrate the process of disconnecting the coupling halves 200 and 300. The components of the fluid coupling assembly 100 are designed so that the steps described below for disconnecting the coupling halves 200 and 300 can only be performed in the sequence described. That is, the fluid coupling assembly 100 includes mechanical structures that prevent any of the steps from being performed out of sequence. Moreover, when a step is completely performed, the step cannot be reversed. The fluid coupling assembly 100 includes mechanical structures that latch the components in the various positions associated with the completion of each of the sequential steps of the disconnection process.

The sequence of steps to disconnect the coupling halves 200 and 300 will ensure that the fluid flow paths of the coupling halves 200 and 300 are fluidly sealed closed prior to the separation of the coupling halves 200 and 300.

Accordingly, the fluid flow paths of the coupling halves 200 and 300 are prevented from becoming contaminated. In addition, no fluid (or only minimal fluid) is spilled when the coupling halves 200 and 300 are separated.

Figure 4:
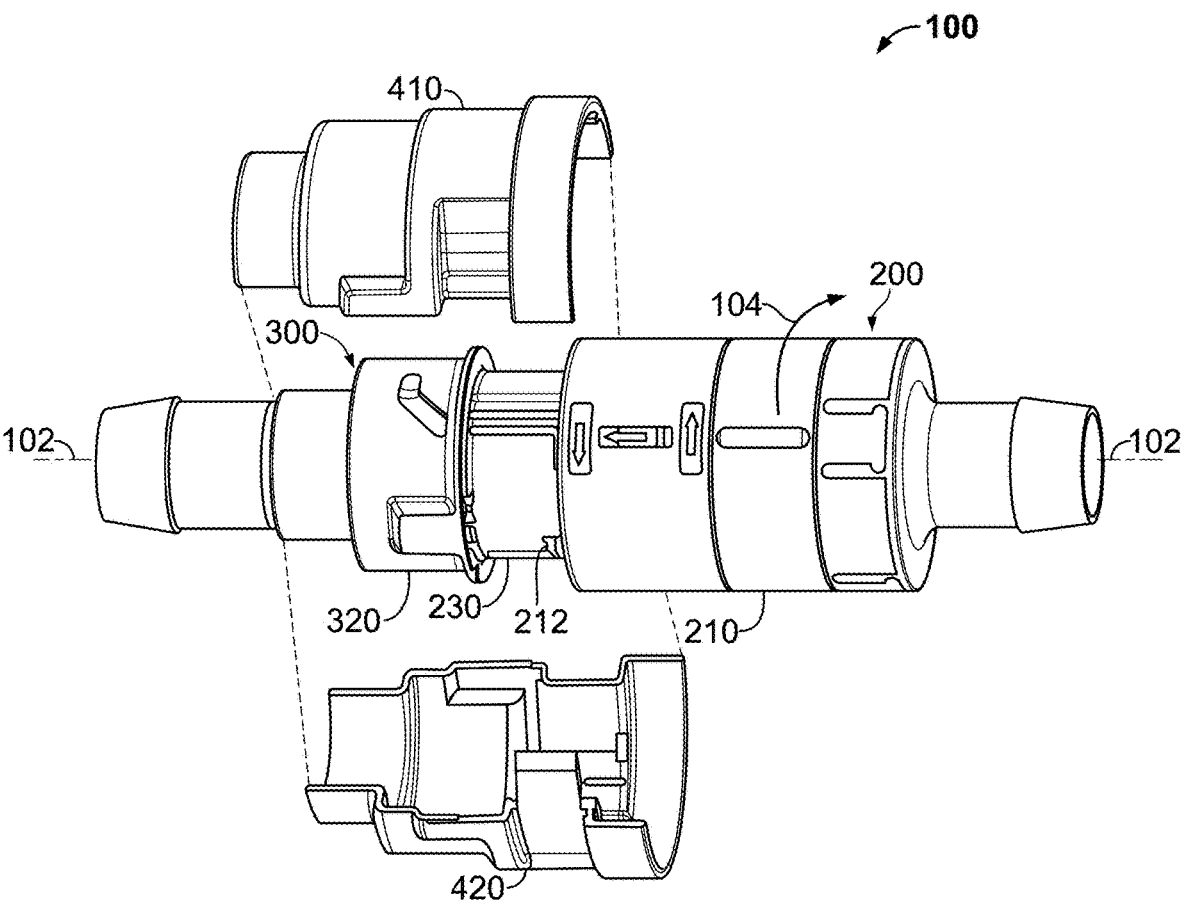
FIG. 4 is a perspective view of the fluid coupling assembly of FIG. 1 arranged in the operative connected configuration with the removable sleeve removed.

First, as illustrated in FIG. 4, the removable sleeve 400 is uncoupled from the coupling halves 200 and 300. The removable sleeve 400 can be considered an anti-tamper sleeve or anti-taper guard because while the removable sleeve 400 is coupled to the coupling halves 200 and 300 no other step for disconnecting the coupling halves 200 and 300 can be performed. Accordingly, the uncoupling of the removable sleeve 400 from the coupling halves 200 and 300 must be the first step in the sequence of steps required to disconnect the coupling halves 200 and 300.

In the depicted embodiment, the removable sleeve 400 includes a first sleeve portion 410 and a second sleeve portion 420. In the depicted embodiment, the first sleeve portion 410 and the second sleeve portion 420 are identical to each other. In some embodiments, the first sleeve portion 410 and the second sleeve portion 420 are different from each other. In particular embodiments, the removable sleeve 400 can be a single item (e.g., a tear-away sleeve). Prior to the removal from the coupling halves 200 and 300, the first sleeve portion 410 and the second sleeve portion 420 are releasably latched to each other using one or two latches (e.g., one or more). To uncouple the removable sleeve 400 from the coupling halves 200 and 300, a user will disengage the latch(es) of the removable sleeve 400 and then separate the first sleeve portion 410 and the second sleeve portion 420 from the coupling halves 200 and 300. In some embodiments, the latch(es) of the removable sleeve 400 become deformed so that once the removable sleeve 400 is uncoupled from the coupling halves 200 and 300, the removable sleeve 400 cannot be recoupled to the coupling halves 200 and 300. With the removable sleeve 400 uncoupled from the coupling halves 200 and 300, it can be seen that the first housing 210 is spaced apart from the second collar 320, while the first sleeve 230 is releasably coupled to the second collar 320.

The second step of the disconnection process is depicted by the arrow 104 in FIG. 4. That is, the first housing 210 (and the components fixedly attached thereto as described below) is/are manually rotated relative to a first sleeve 230 of the first coupling 200 and relative to the second coupling 300. In particular, the first housing 210 is manually rotated about the longitudinal axis 102 relative to the first sleeve 230 and the second coupling 300. This step cannot be performed prior to the uncoupling of the removable sleeve 400 from the coupling halves 200 and 300 because the removable sleeve 400 includes mechanical elements that engage with each of the coupling halves 200 and 300 to prevent the rotation of the first coupling 200 relative to the second coupling 300 as depicted by the arrow 104. In some embodiments, the rotation of the first housing 210 relative to the second coupling 300 can be limited to a range of about 5° to 20°, or about 5° to 30°, or about 5° to 45°, without limitation.

The fluid flow path 103 (see FIG. 3) remains open during and after each of the first and second steps of the disconnection process.

Figure 5:
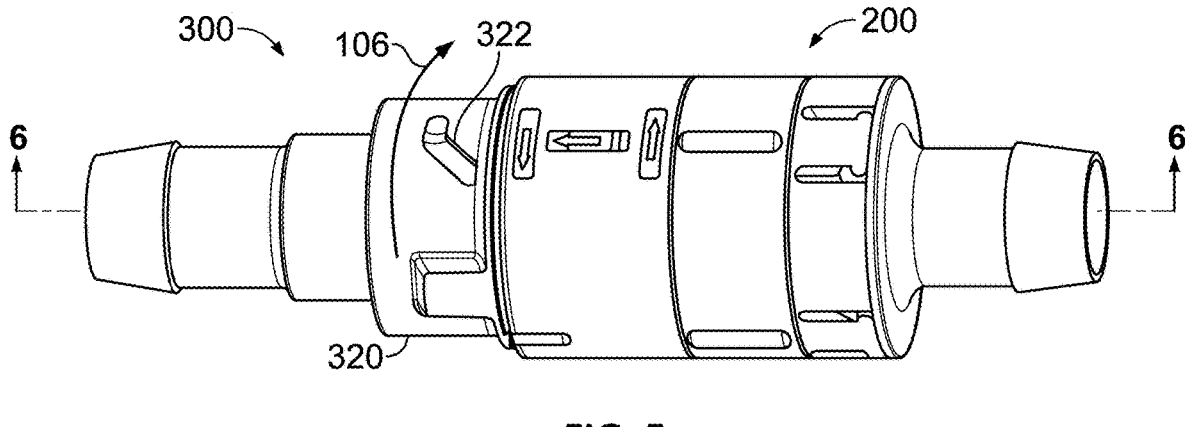
FIG. 5 is a perspective view of the fluid coupling assembly of FIG. 4 in a longitudinally compressed arrangement in preparation for disconnection of the two couplings that make up the fluid coupling assembly.
Figure 6:
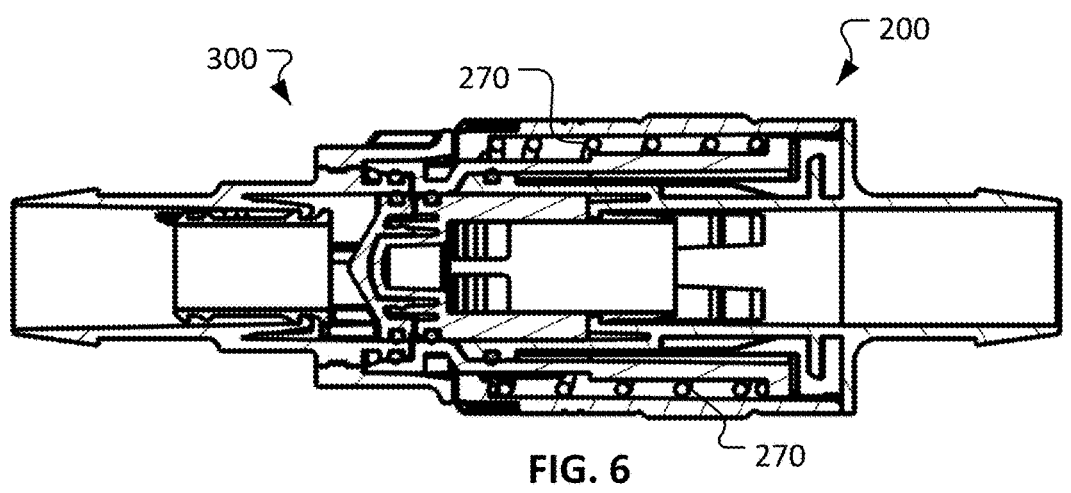
FIG. 6 is a longitudinal cross-sectional view of the fluid coupling assembly of FIG. 5 taken along the break line 6-6.

Referring to FIGS. 5 and 6, after the rotation of the first coupling 200 relative to the second coupling 300, the first coupling 200 can then be translated toward the second coupling 300 (along the longitudinal axis 102) to arrive at the configuration shown in FIGS. 5 and 6. This translation of the first coupling 200 and the second coupling 300 toward each other is the third step of the disconnection process.

At the completion of this third step of the disconnection process, the flow paths through the first coupling 200 and the second coupling 300 are each fluidly sealed in a closed state. That is, the flow paths through the first coupling 200 and the second coupling 300 are each fluidly sealed closed in the depicted configuration, which is prior to the separation of the coupling halves 200 and 300.

In the depicted embodiment, the first coupling 200 includes a compression spring 270 that, after the rotation of the first coupling 200 relative to the second coupling 300 as indicated by the arrow 104 (FIG. 4), is released to extend. The extension of the spring 270 forcibly assists with the longitudinal translation of the first coupling 200 toward the second coupling 300. This mechanical assistance by the spring 270 can be beneficial because otherwise, at least in some embodiments, a substantial amount of force would be required by the user to cause the longitudinal translation of the first coupling 200 toward the second coupling 300 (e.g., to overcome the sliding friction from the multiple seals).

As described further below, the first coupling 200 and the second coupling 300 each include an internal valve. The valves of the first coupling 200 and the second coupling 300 are each open (to allow the fluid flow path 130 to be open through the fluid coupling assembly 100, as shown in FIG. 3 for example) until the first coupling 200 and the second coupling 300 are transitioned into the configuration shown in FIGS. 5 and 6. The act of translating the first coupling 200 and the second coupling 300 toward each other also concurrently causes the joint translation of the internal valves to move to positions that fluidly close and seal the flow paths through the couplings 200 and 300. The internal valves lock in the closed positions to prevent the valves from ever opening again.

The fourth step of the disconnection process is depicted by the arrow 106 shown in FIG. 5. That is, to perform the fourth step a user will manually rotate the second coupling 300 relative to the first coupling 200. In particular, the second coupling 300 needs to be manually rotated about the longitudinal axis 102 relative to the first coupling 200.

As described further below, the first coupling 200 and the second coupling 300 include mechanical structural elements that prevent this fourth step from even being possible prior to the translation of the translation of the first coupling 200 and the second coupling 300 toward each other (i.e., the third step of the disconnection process).

As visible in FIG. 5, the second coupling 300 includes a second collar 320 that defines one or more slots 322 (e.g., two slots 322 in the depicted embodiment). A radial projection of the first coupling 200 is slidably disposed in each of the one or more slots 322. At least a portion of the one or more slots 322 extends at an acute angle relative to the longitudinal axis 102. Accordingly, as the second coupling 300 is manually rotated about the longitudinal axis 102 relative to the first coupling 200, the projection(s) travels in the slot(s) 322 along the acute angle, which causes the first coupling 200 and the second coupling 300 to longitudinally separate from each other. Since the internal valves of the first coupling 200 and the second coupling 300 became closed as a result of the third step (as described above), the first coupling 200 and the second coupling 300 can be separated from each other without any potential of contaminating the flow paths within the first coupling 200 and the second coupling 300.

Figure 7:
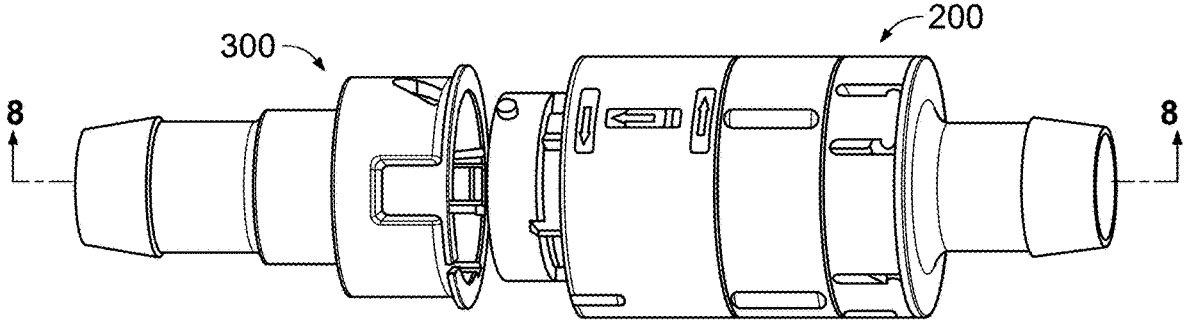
FIG. 7 is a perspective view of the fluid coupling assembly of FIG. 4 with the two couplings that make up the fluid coupling assembly being disconnected from each other.
Figure 8:
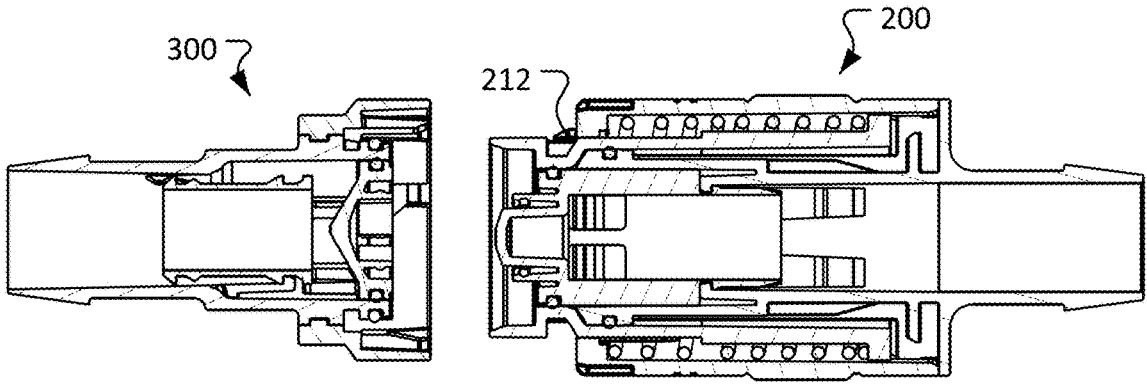
FIG. 8 is a longitudinal cross-sectional view of the fluid coupling assembly of FIG. 7 taken along the break line 7-7.

Referring to FIGS. 7 and 8, here the first coupling 200 and the second coupling 300 are separated from each other. This is the completion of the multi-step disconnection process. As the first coupling 200 and the second coupling 300 are separated from each other, no fluid (or minimal amounts of fluid) is spilled into the environment. That is the case because the internal valves are in their closed positions, and because there are essentially no fluid-containing spaces between the first coupling 200 and the second coupling 300. For example, as described further below, the front faces of the internal valve members are sealed against each other. In addition, the first coupling 200 and the second coupling 300 do not define open spaces and include other seals that also contribute to the no-spill functionality of the first coupling 200 and the second coupling 300.

Figures 9, 10:
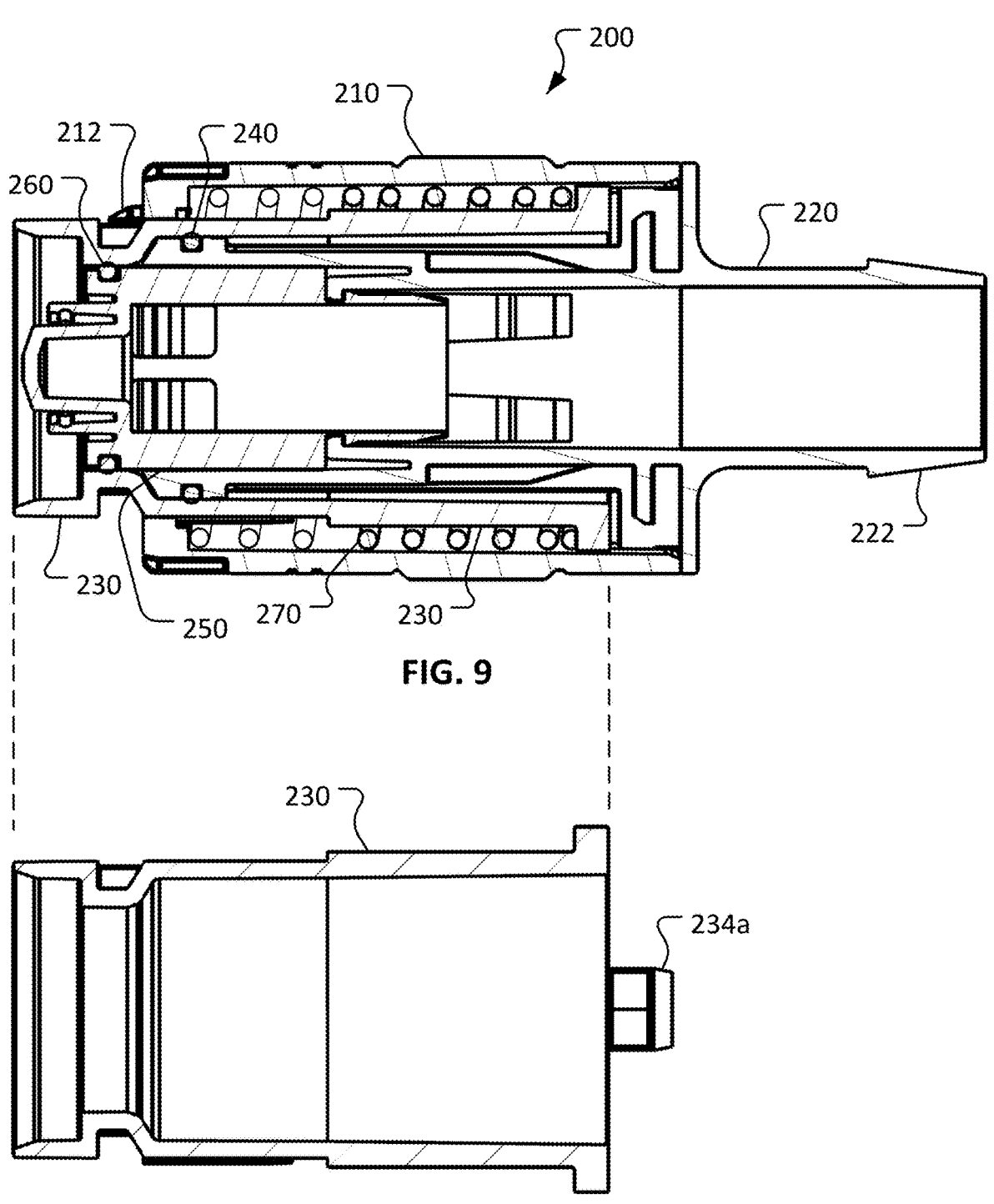
FIG. 9 is a longitudinal cross-sectional view of a first coupling of the fluid coupling assembly of FIG. 1.
FIG. 10 is a longitudinal cross-sectional view of a sleeve component of the first coupling of FIG. 9.

FIG. 9 shows the first coupling 200 in isolation so that its components can be described in greater detail. In the depicted embodiment, the first coupling 200 includes a first housing 210, a first termination and plunger member 220, a first sleeve 230, a plunger seal 240, a first valve 250, a first valve seal 260, and a spring 270.

The first housing 210 is fixedly coupled with: (i) the first termination and plunger member 220 and (ii) the first valve 250. Accordingly, for practical purposes the first housing 210, the first termination and plunger member 220, and the first valve 250 function unitarily as a single component. In some embodiments, these components can be snapped together during the assembly process of the first coupling 200. Other joining techniques can also be used (e.g., ultrasonic welding, using adhesive, threading, etc.).

The first sleeve 230 is slidably disposed inside of the first housing 210. The first sleeve 230 is also slidably disposed around the first termination and plunger member 220 and the first valve 250. The first sleeve 230 is slidable with respect to the first housing 210, the first termination and plunger member 220, and the first valve 250 between a first configuration and a second configuration. In the first configuration, the first sleeve 230 is extended from the first housing 210, the first termination and plunger member 220, and the first valve 250 (e.g., as shown in FIG. 3). In this first configuration, the flow path 103 is open through the first coupling 200. In the second configuration, the first sleeve 230 is retracted relative to the first housing 210, the first termination and plunger member 220, and the first valve 250 (e.g., as shown in FIG. 9). In this second configuration, the flow path 103 through the first coupling 200 is sealed closed.

The spring 270 is disposed between the first sleeve 230 and the first housing 210. The spring 270 extends longitudinally and has a central axis coincident with the longitudinal axis 102 of the first coupling 200. One end of the spring 270 is abutted against the first housing 210, and the opposite end of the spring 270 is abutted against the first sleeve 230. Accordingly, the spring 270 biases the first sleeve 230 toward its second configuration in which the flow path 103 through the first coupling 200 is sealed closed.

The plunger seal 240 is disposed between the first termination and plunger member 220 and the first sleeve 230. In the depicted embodiment, the plunger seal is seated in an annular groove defined by the first termination and plunger member 220. The plunger seal 240 abuts against the inner diameter of the first sleeve 230. As the first sleeve 230 reconfigures from its first configuration to its second configuration, the plunger seal 240 slides along the inner wall surface of the first sleeve 230.

The first valve seal 260 is disposed in an annular groove defined by the first valve 250. When the first sleeve 230 is in its first configuration (i.e., extended relative to the first housing 210, the first termination and plunger member 220, and the first valve 250 as shown in FIG. 3), the first valve seal 260 is only in contact with the first valve 250. The outer diameter of the first valve seal 260 is not in contact with anything. Then, as the first sleeve 230 retracts toward the first housing 210, the first termination and plunger member 220, and the first valve 250, the first valve seal 260 comes into contact with a portion of the inner wall of the first sleeve 230 (as shown in FIG. 9). In that position, the first valve seal 260 fluidly seals the fluid flow path closed within the first coupling 200.

Figure 11:
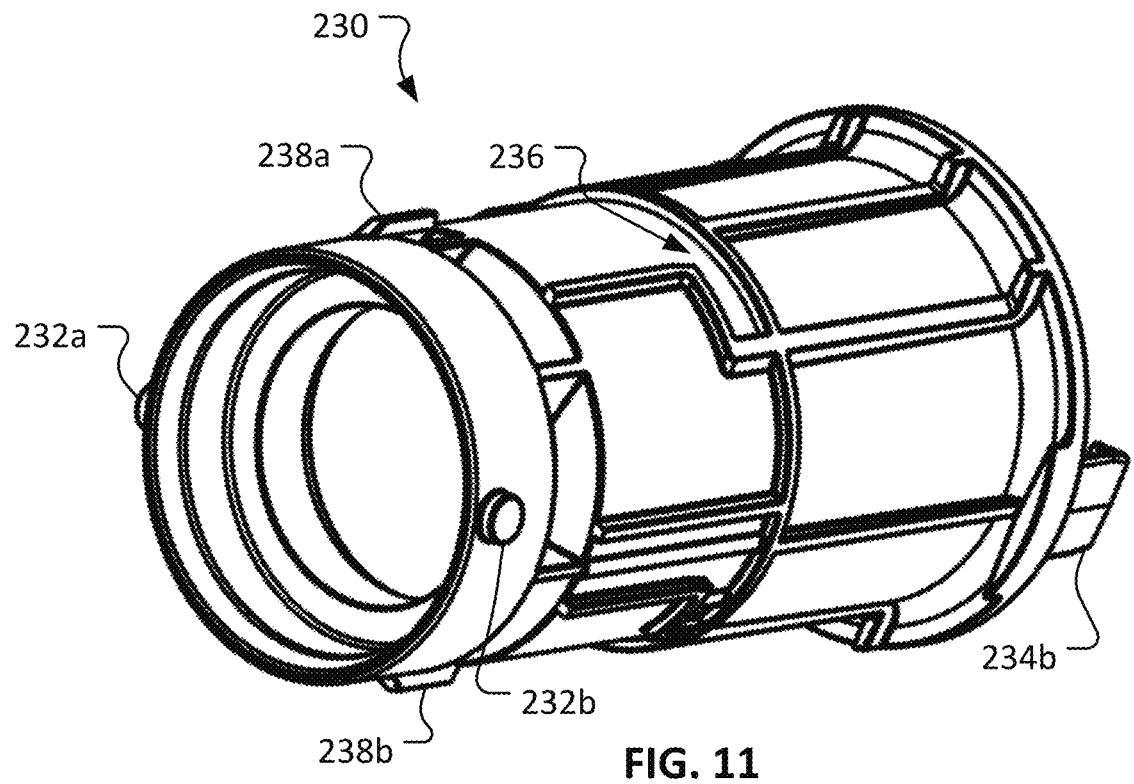
FIG. 11 is a perspective view of the sleeve component of FIG. 9.
Figure 12:
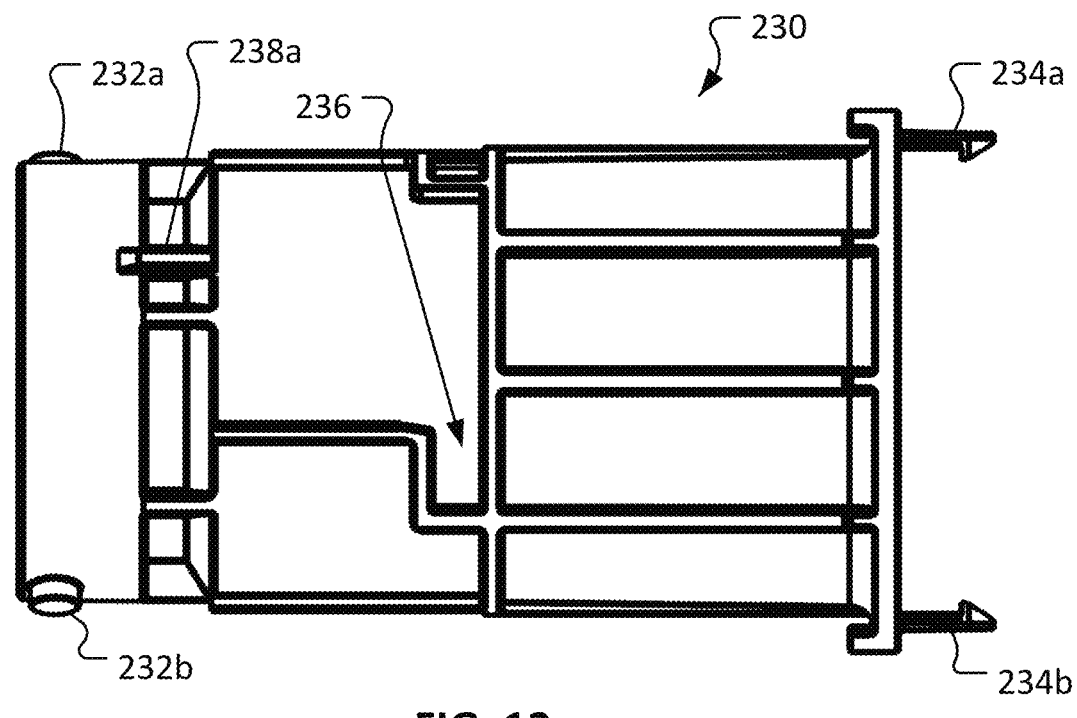
FIG. 12 is a side view of the sleeve component of FIG. 9.

FIGS. 10-12 show the first sleeve 230 in isolation so that more details are readily visible. For example, the first sleeve 230 includes two radial projections 232a and 232b. While the first coupling 200 is engaged with the second coupling 300, these radial projections 232a-b are each slidably disposed within a respective one of the slots 322 defined by the second collar 230 of the second coupling 300.

The first sleeve 230 also includes two deflectable latch members 234a and 234b. These latch members 234a-b snap into engagement with the first termination and plunger member 220 at the end of the third disconnection step during which the first coupling 200 and the second coupling 300 are translated toward each other (with the help from the spring 270). Accordingly, at the end of this step, the deflectable latch members 234a-b lock the first sleeve 230 in its retracted second configuration in which the first valve seal 260 fluidly seals the fluid flow path closed within the first coupling 200.

The outer surface of the first sleeve 230 also defines one or more circumferentially extending slots 236. Each of the slots 230 receives a radially inward extending projection of the first housing 210. The engagement between the radially inward extending projections of the first housing 210 and the slots 230 keep the first coupling 200 and the second coupling 300 in the arrangement shown in FIG. 4 (with the open fluid flow path 103 as shown in FIG. 3) after the uncoupling of the removable sleeve 400. Then, as the first coupling 200 is manually rotated relative to the second coupling 300 as indicated by the arrow 104 (FIG. 4), the radially inward extending projections of the first housing 210 slide circumferentially within the slots 230. When the relative rotation is executed to the extent that the radially inward extending projections of the first housing 210 exit the circumferentially extending slots 236, then the second step of the disconnection process has been completed. Then the third disconnection step during which the first coupling 200 and the second coupling 300 are translated toward each other (with the help from the spring 270) can be performed (once the radially inward extending projections of the first housing 210 have exited the circumferentially extending slots 236).

The outer surface of the first sleeve 230 also includes two radial projections 238a and 238b. As described further below, when the fluid coupling assembly 100 is in its operable configuration each of these radial projections 238a-b abuts against a cantilever spring 324 of the second collar 320 of the second coupling 300. The abutment between the radial projections 238a-b and the cantilever springs 324 acts as a lock mechanism that prevents any relative rotation between the first coupling 200 and the second coupling 300. This lock mechanism is released at the end of the third step of the disconnection process when the ramp members 212 of the first housing 210 (e.g., see FIGS. 4, 8, and 9) deflect the cantilever springs 324 radially outward so that they clear the tops of the radial projections 238a-b.

Figure 13:
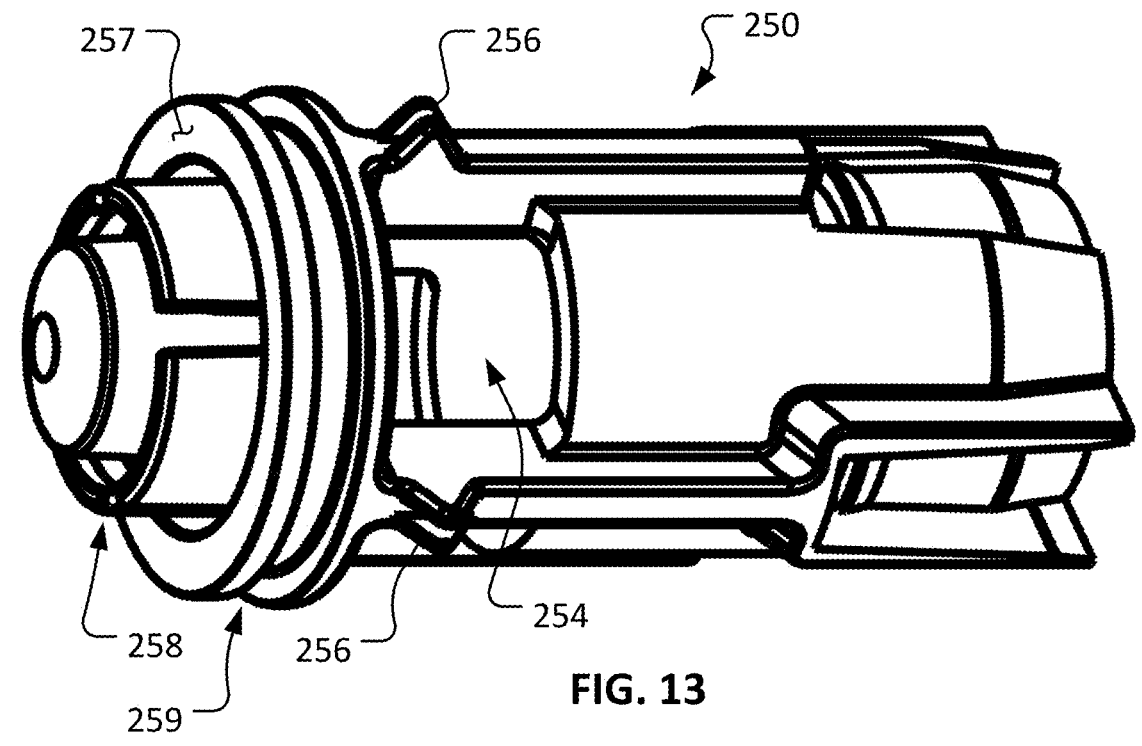
FIG. 13 is a perspective view of a valve component of the first coupling of FIG. 9.
Figure 14:
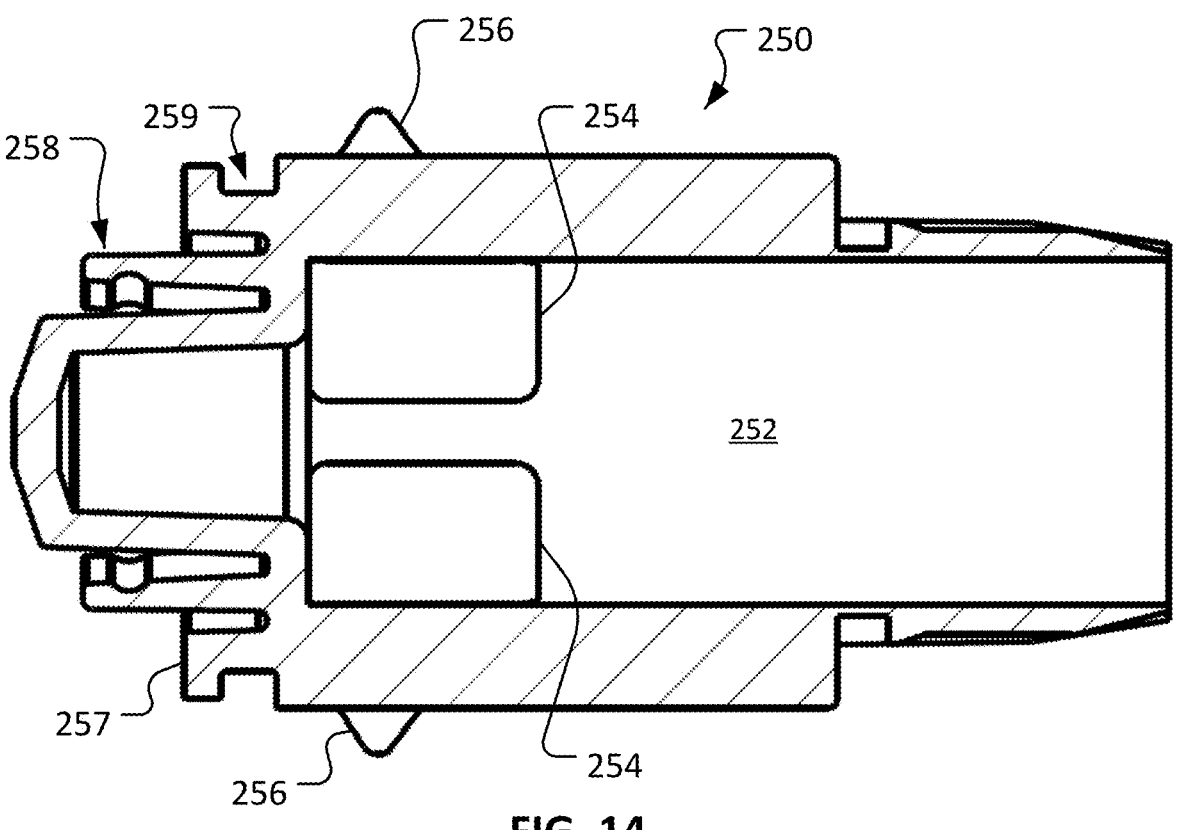
FIG. 14 is a longitudinal cross-sectional view of the valve component of FIG. 13.

FIGS. 13 and 14 show the first valve 250 in isolation so that more details are readily visible. For example, the first valve 250 defines an open interior space 252. The first valve 250 also defines one or more wall openings or fenestrations 254 (four fenestrations 254 in the depicted embodiment).

The fluid flow path 103 (FIG. 3) extends through the open interior space 252 and through the one or more fenestrations 254.

The first valve 250 also includes multiple radially outward extending hard stop members 256. At the end of the third step of the disconnection process (when the first coupling 200 and the second coupling 300 translate toward each other), the hard stop members 256 come into contact with and abut against corresponding surfaces of the first sleeve 230 to stop the travel of the first valve 250 relative to the first sleeve 230 in a position in which the first valve seal 260 fluidly seals the fluid flow path closed within the first coupling 200.

The first valve 250 also includes a latch mechanism 258. The latch mechanism 258 releasably latches the first valve 250 to the second valve 330 (i.e., the second valve 330 of the second coupling 300). Such latching between the first valve 250 and the second valve 330 ensures that the first valve 250 to the second valve 330 remain closely conjoined, face-to-face, until the first coupling 200 is separated from the second coupling 300. The unlatching of the first valve 250 from the second valve 330 takes place during the fourth step of the disconnection process (depicted by the arrow 106 shown in FIG. 5). As the second coupling 300 is manually rotated about the longitudinal axis 102 relative to the first coupling 200, the radial projections 232a travel in the slot(s) 322 of the second collar 320 along the acute angle defined by the slot(s) 322, which overcomes the latching force provided by the latch mechanism 258, and the causes the unlatching of the first valve 250 from the second valve 330.

The first valve 250 also includes a front face surface 257 and defines an annular seal groove 259.

Figures 15, 16:
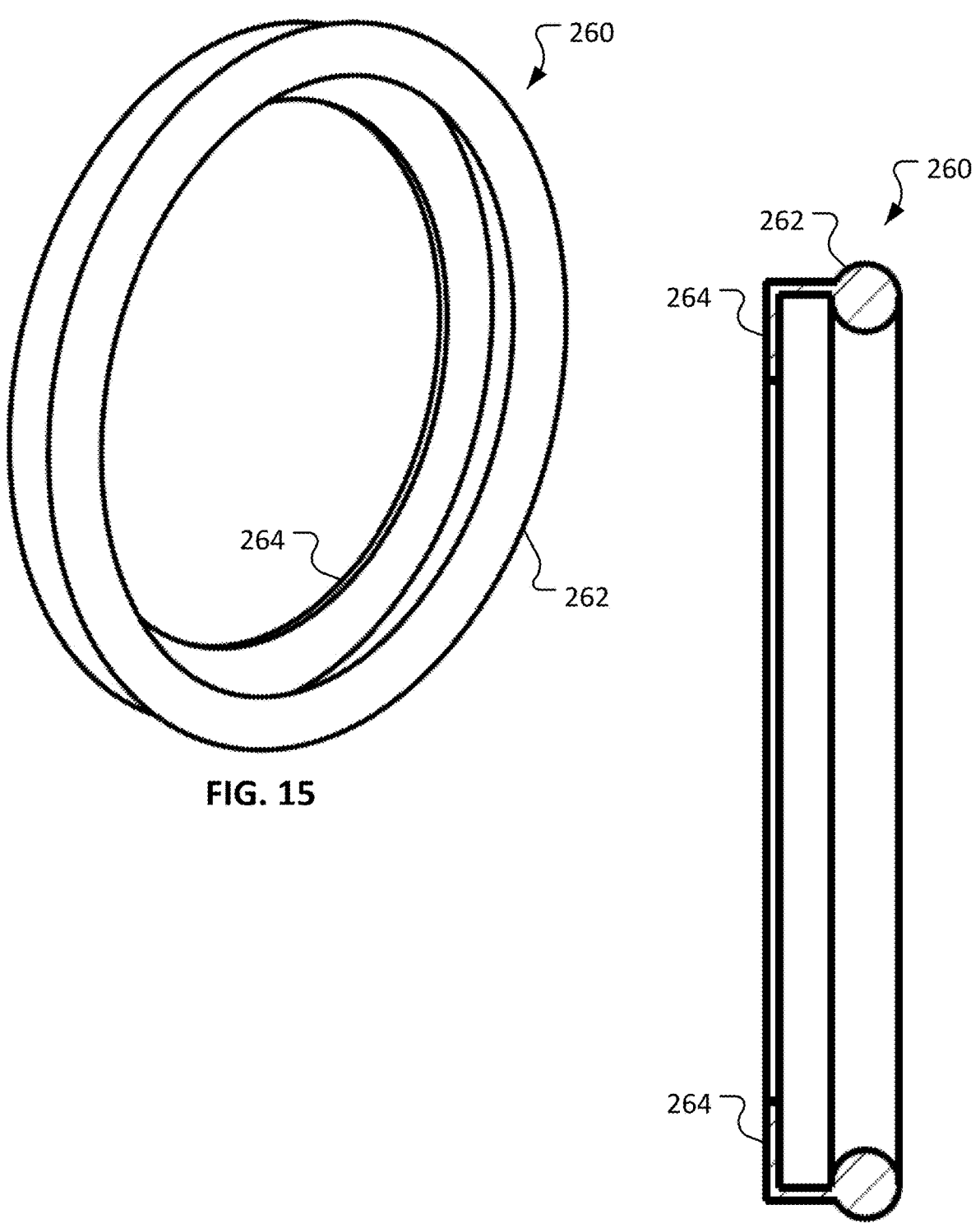
FIG. 15 is a perspective view of a valve seal component of the first coupling of FIG. 9.
FIG. 16 is a longitudinal cross-sectional view of the valve seal component of FIG. 15.

FIGS. 15 and 16 show the first valve seal 260 in isolation so that more details are readily visible. For example, the first valve seal 260 includes an annular seal portion 262 and a face seal portion 264. When the first valve seal 260 is coupled to the first valve 250, the annular seal portion 262 is seated in the annular seal groove 259. In that position, the annular seal portion 262 of the first valve seal 260 seals against the first sleeve 230 when the first sleeve 230 is in its second, retracted configuration.

The face seal portion 264 of the first valve seal 260 covers the front face surface 257 of the first valve 250. In that position, the face seal portion 264 resides between the front faces of the first valve 250 and the second valve 330. The latch mechanism 258 of the first valve 250 ensures that there is a light longitudinal compression of the face seal portion 264 between the front faces of the first valve 250 and the second valve 330. Accordingly, no fluid can reside between the front faces of the first valve 250 and the second valve 330 as long as the first valve 250 and the second valve 330 are latched together via the latch mechanism 258. This provides a non-spill functionality upon disconnection.

Figures 17, 18:
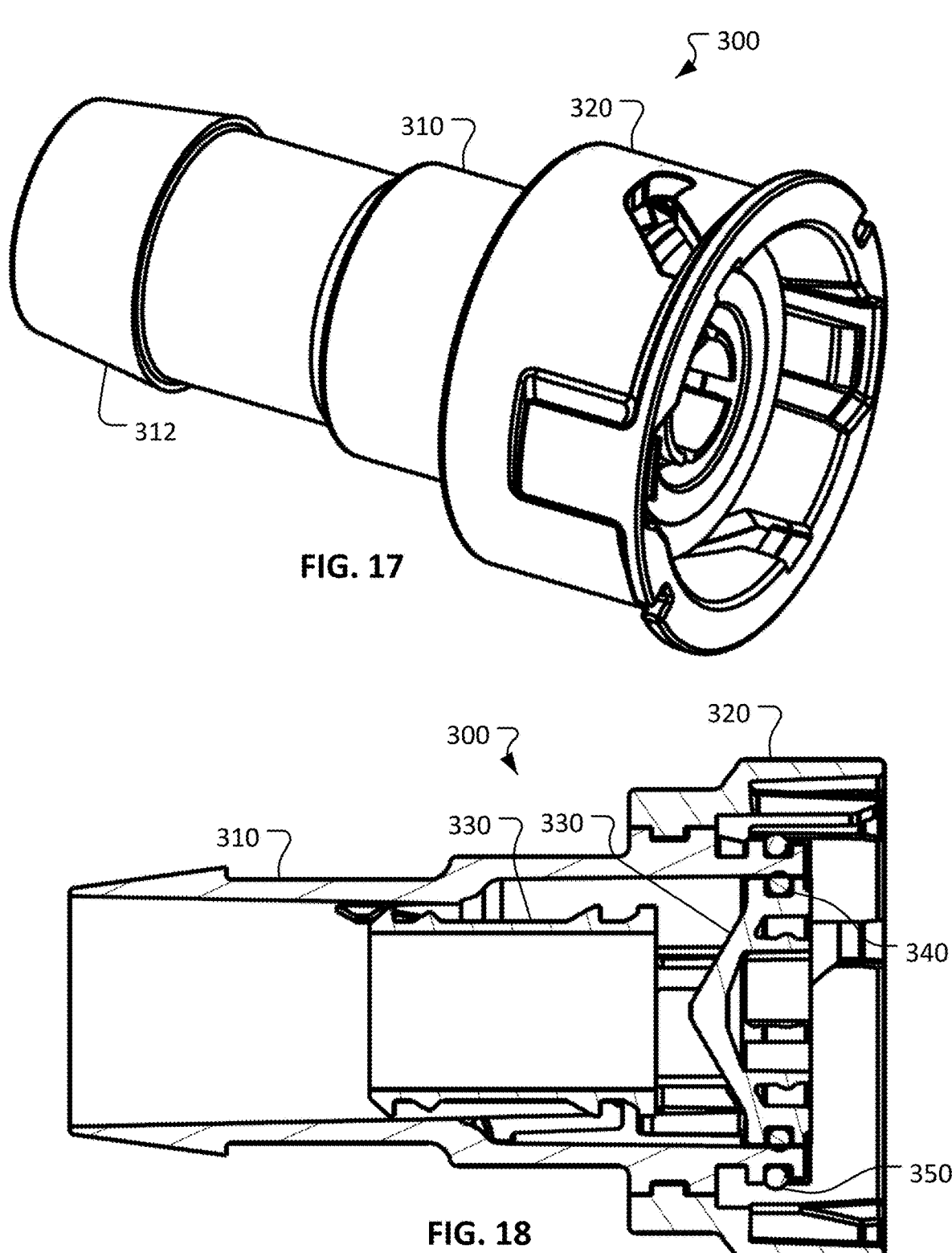
FIG. 17 is a perspective view of a second coupling of the fluid coupling assembly of FIG. 1.
FIG. 18 is a longitudinal cross-sectional view of the second coupling of FIG. 17.

FIGS. 17 and 18 show the second coupling 300 in isolation so that more details are readily visible. For example, the second coupling 300 includes a second termination member 310, a second collar 320, a second valve 330, a second valve seal 340, and a second coupling seal 350.

The second termination member 310 and the second collar 320 are fixedly attached to each other and function unitarily as a single component. In some embodiments, these components can be snapped together during the assembly process of the second coupling 300. Other joining techniques can alternatively be used (e.g., ultrasonic welding, using adhesive, threading, etc.), or the second termination member 310 and the second collar 320 can be constructed unitarily.

The second valve 330 is slidably disposed within the second termination member 310. The second valve 330 is shown in FIG. 18 in its second retracted configuration. In the second retracted configuration of the second valve 330, the fluid flow path through the second coupling 300 is closed and fluidly sealed. FIG. 3 shows the second valve 330 in its first extended configuration. When the second coupling 300 is in its first extended configuration the fluid flow path 103 is open through the second coupling 300. The disconnection process of the fluid coupling assembly 100 as described above causes the reconfiguration of the second valve 330 from its initial first extended configuration to its final second retracted configuration. In particular, the reconfiguration of the second valve 330 from its extended configuration to its retracted configuration takes place during the third step of the disconnection process (i.e., the translation of the first coupling 200 and the second coupling 300 toward each other).

The second coupling 300 also includes the second valve seal 340. The second valve seal 340 is an annular seal that is disposed between the second valve 330 and the inner wall of the second termination member 310. The second valve seal 340 provides the fluid seal to close the fluid flow path through the second coupling 300 when the second valve 330 is in its second retracted configuration as shown.

The second coupling 300 also includes the second coupling seal 350. The second coupling seal 350 provides a fluid seal between the second termination member 310 and the first sleeve 230. The second coupling seal 350 actually provides two seals in the coupled state (i.e., both a face seal and a circumferential radial seal against the first sleeve 230).

Figures 19, 20:
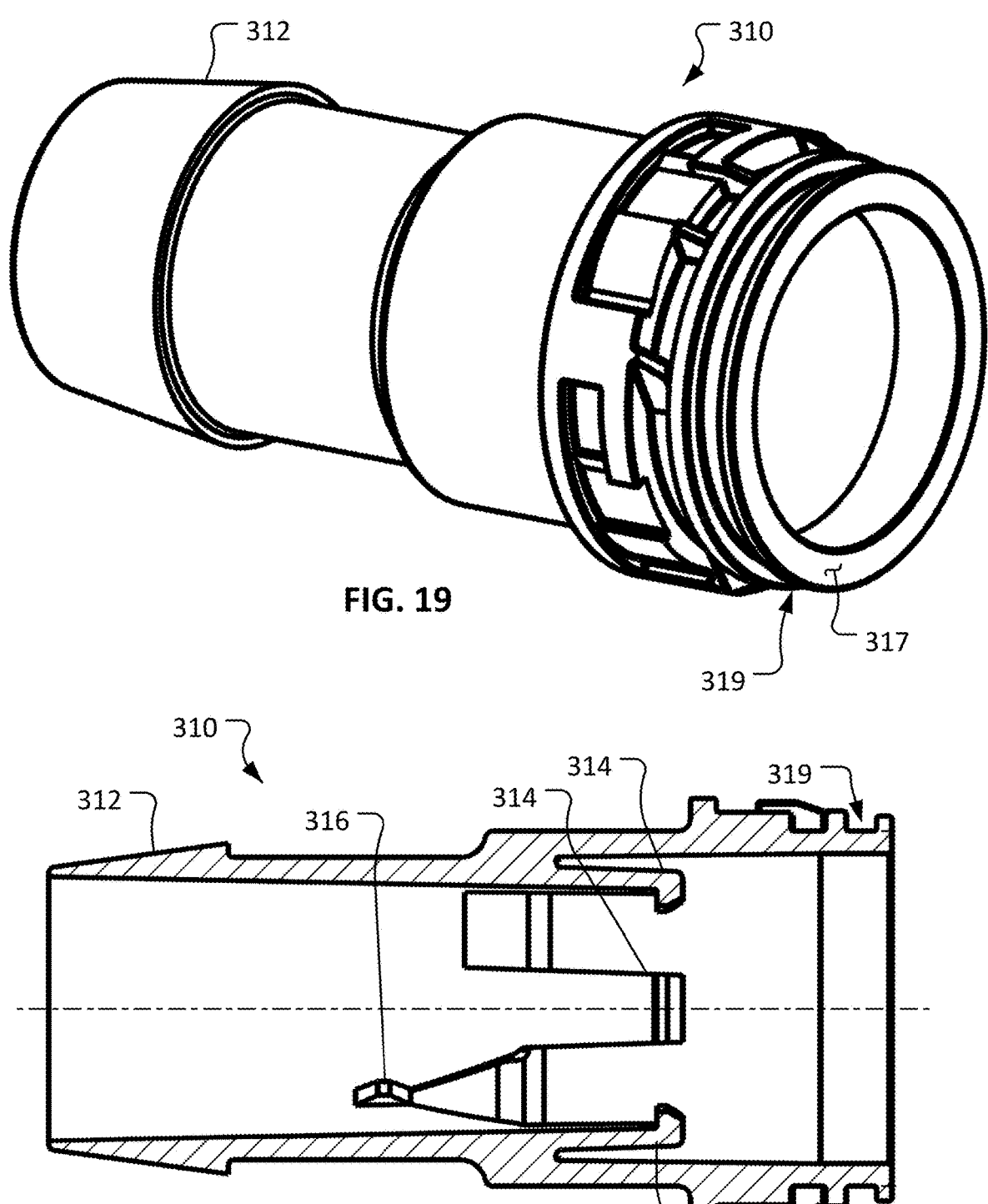
FIG. 19 is a perspective view of a termination member component of the second coupling of FIG. 17.
FIG. 20 is a longitudinal cross-sectional view of the termination member component of FIG. 19.

FIGS. 19 and 20 show the second termination member 310 in isolation so that more details are readily visible. For example, the second termination member 310 includes the second termination 312, one or more pawls 314, one or more hard stop protrusions 316, a front face surface 317, and an annular seal groove 319. The one or more pawls 314 (there are four pawls 314 in the depicted embodiment) are cantilever springs with teeth at the free end of the cantilever springs. The teeth of the one or more pawls 314 engage in annular grooves of the second valve 330 as described below.

The one or more hard stop protrusions 316 (there are two hard stop protrusions 316 in the depicted embodiment) project radially inward from the inner wall of the second termination member 310. The one or more hard stop protrusions 316 limit the translation of the second valve 330 to thereby define the second retracted configuration of the second valve 330.

Figures 21, 22:
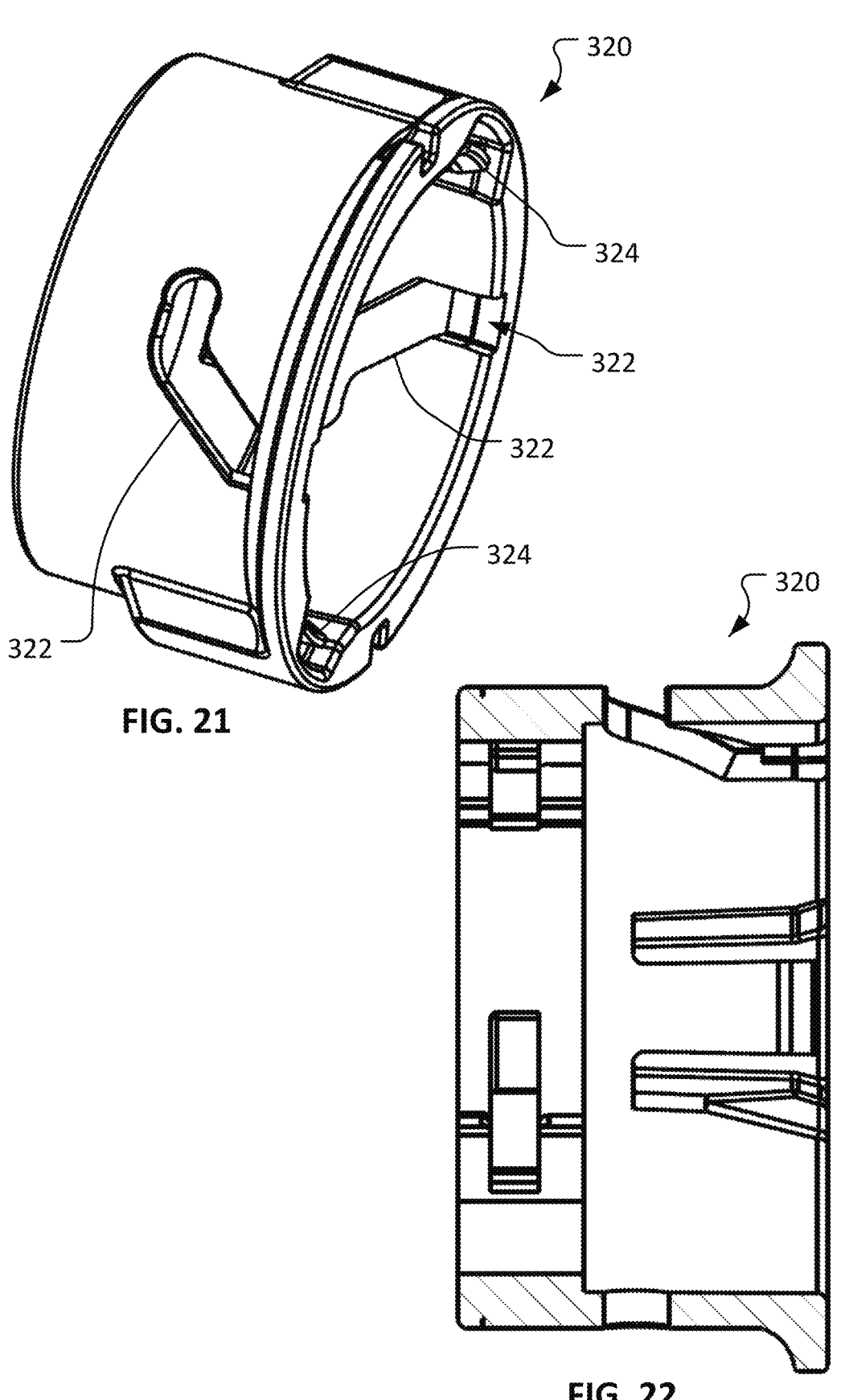
FIG. 21 is a perspective view of a of a collar component of the second coupling of FIG. 17.
FIG. 22 is a longitudinal cross-sectional view of the collar component of FIG. 21.

FIGS. 21 and 22 show the second collar 320 in isolation so that more details are readily visible. For example, the second collar 320 defines the one or more slots 322 (two slots 322 in the depicted embodiment). Those slots 322 include: (i) a circumferentially extending portion, (ii) a portion that extends along an acute angle relative to the longitudinal axis 102, and (iii) a longitudinally extending portion that has an open end. The radial projections 232a-b are slidably disposed in the slots 322. In the functional configuration (e.g., as shown in FIG. 3), the radial projections 232a-b reside in the circumferentially extending portion of the slots 322. During the fourth step of the disconnection process, the radial projections 232a-b travel along the portion that extends along an acute angle relative to the longitudinal axis 102 (as a user manually rotates the second coupling 300 relative to the first coupling 200). Then, after the rotation, the radial projections 232a-b enter the longitudinally extending portion of the slots 322 and exit the open ends of the slots 322 to fully disconnect the first coupling 200 from the second coupling 300.

The second collar 320 also has one or more cantilever springs 324 (e.g., two cantilever springs 324 are included in the depicted embodiment). The cantilever springs 324 are locking mechanisms that prevent any rotation of the second coupling 300 relative to the first coupling 200 until and unless step three of the disconnection process has been completed. Said another way, the one or more cantilever springs 324 engage against the two radial projections 238a and 238b to prevent step four of the disconnection process from being started until step three of the disconnection process has been completed. To deactivate the locking functionality provided by the one or more cantilever springs 324 and the projections 238a-b, the ramp members 212 of the first housing 210 (e.g., see FIGS. 4, 8, and 9) contact and deflect the one or more cantilever springs 324 radially outward so that they clear the tops of the radial projections 238a-b when the first coupling 200 and second coupling 300 have been fully translated toward each other at the end of step three of the disconnection process.

Figures 23, 24:
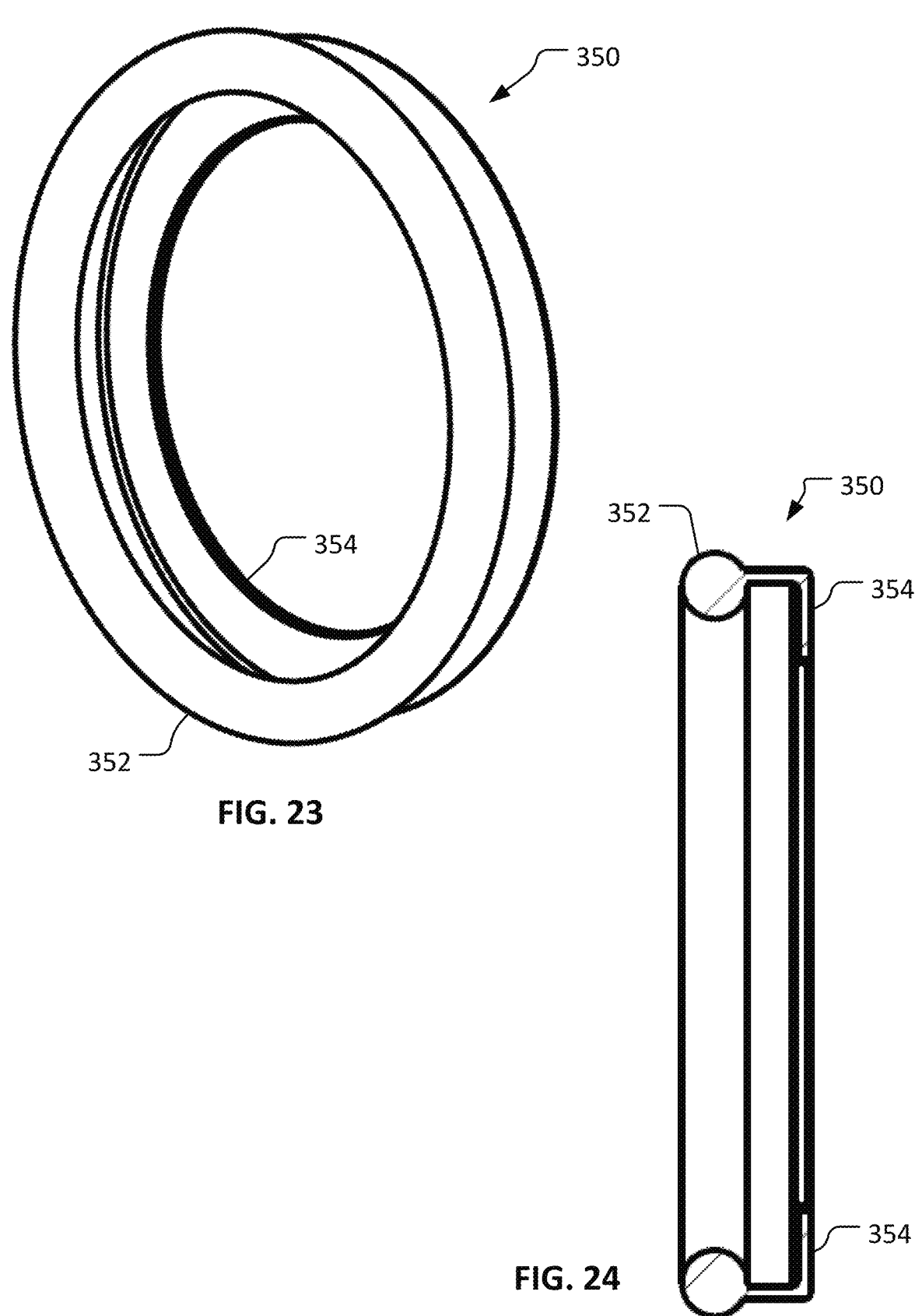
FIG. 23 is a perspective view of a coupling seal component of the second coupling of FIG. 17.
FIG. 24 is a longitudinal cross-sectional view of the coupling seal component of FIG. 23.

FIGS. 23 and 24 show the second coupling seal 350 in isolation so that more details are readily visible. For example, the second coupling seal 350 includes an annular seal portion 352 and a face seal portion 354. When the second coupling seal 350 is coupled to the second termination member 310, the annular seal portion 352 is seated in the annular seal groove 319 and the face seal portion 354 covers the front face surface 317 of the second termination member 310. In that position, both the annular seal portion 352 and the face seal portion 354 seal against the first sleeve 230 of the first coupling 200 (until step four of the disconnection process). That is, the second coupling seal 350 actually provides two seals (i.e., both a face seal and a circumferential radial seal against the first sleeve 230).

Figures 25, 26:
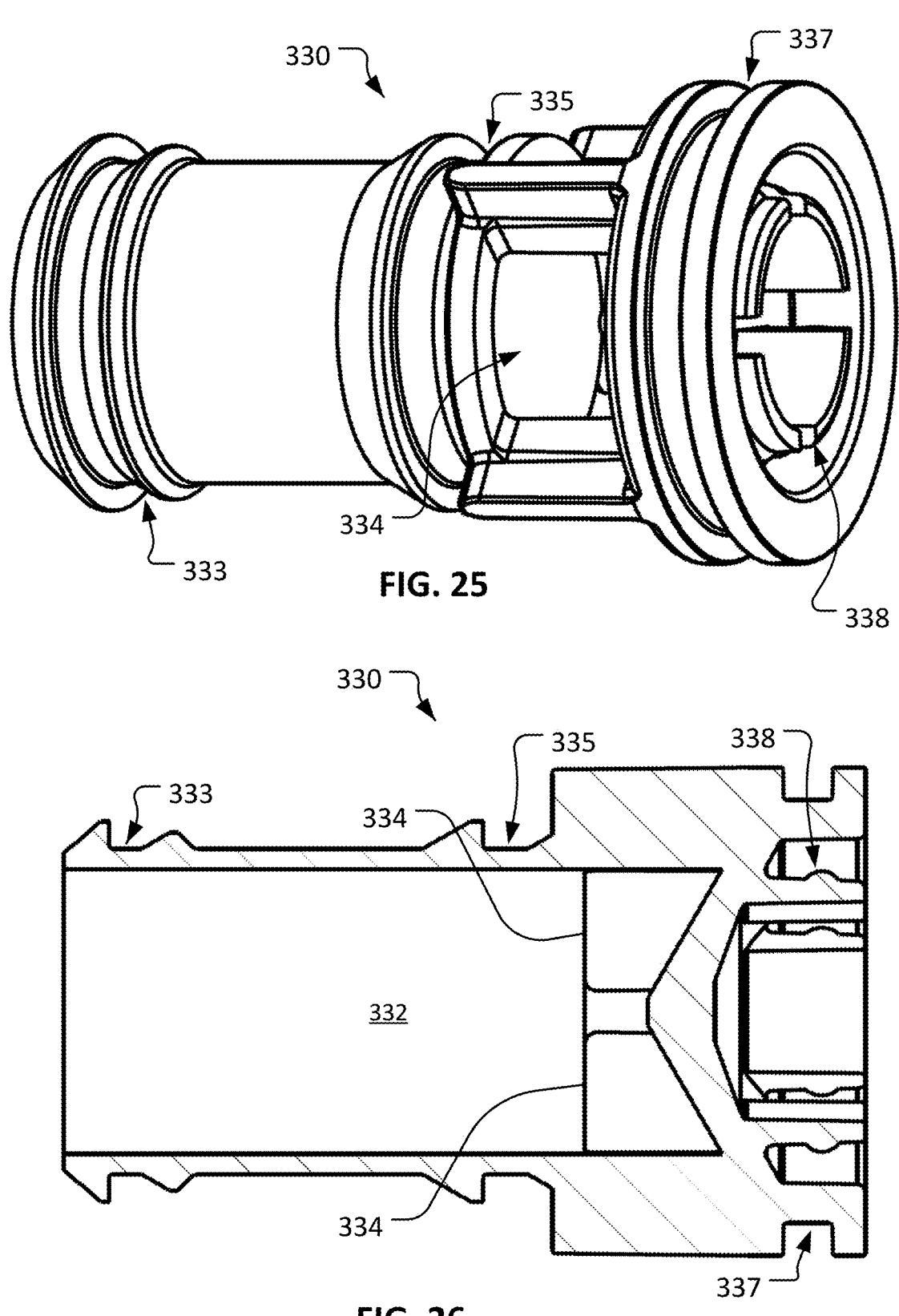
FIG. 25 is a perspective view of a valve component of the second coupling of FIG. 17.
FIG. 26 is a longitudinal cross-sectional view of the valve component of FIG. 25.

FIGS. 25 and 26 show the second valve 330 in isolation so that more details are readily visible. For example, the second valve 330 defines an open interior space 332. The second valve 330 also defines one or more wall openings or fenestrations 334 (four fenestrations 334 in the depicted embodiment). The fluid flow path 103 (FIG. 3) extends through the open interior space 332 and through the one or more fenestrations 334.

The second valve 330 also includes a first annular latch groove 333 and a second annular latch groove 335. When the second valve 330 is in its first extended configuration (e.g., as shown in FIG. 3), one or more pawls 314 (FIG. 20) that extend from the inner wall of the second termination member 310 are releasably engaged in the first annular latch groove 333. Accordingly, the releasable engagement of the one or more pawls 314 of the second termination member 310 in the first annular latch groove 333 allows the second valve 330 to translate from its first extended configuration to its second retracted configuration. However, the releasable engagement of the one or more pawls 314 of the second termination member 310 in the first annular latch groove 333 prevents the second valve 330 from translating in the opposite direction.

When the second valve 330 is in its second retracted configuration (e.g., as shown in FIG. 6), the one or more pawls 314 that extend from the inner wall of the second termination member 310 are permanently engaged in the second annular latch groove 335. In addition, when the second valve 330 is in its second retracted configuration the other end of the second valve 330 abuts against a hard stop protrusion 314 (FIG. 20) that extends from the inner wall of the second termination member 310. Accordingly, the one or more pawls 314 and the hard stop protrusion 314 capture and lock the second valve 330 is in its second retracted configuration.

The second valve 330 also includes an annular seal groove 337 in which the second valve seal 340 is seated. The second valve seal 340 provides a fluid seal between the second valve 330 and the inner wall of the second termination member 310 when the second valve 330 is in its second retracted configuration. This fluid seal provided by the second valve seal 340 closes the fluid flow path through the second valve 330.

The second valve 330 also includes a latch engagement structure 338. The latch engagement structure 338 releasably couples with the latch mechanism 258 of the first valve 250 until the two valves are separated from each other during the execution of step four of the disconnection process. Such latching between the first valve 250 and the second valve 330 ensures that the first valve 250 and the second valve 330 remain closely conjoined, face-to-face, until the first coupling 200 is separated from the second coupling 300. The unlatching of the first valve 250 from the second valve 330 takes place during the fourth step of the disconnection process (depicted by the arrow 106 shown in FIG. 5). As the second coupling 300 is manually rotated about the longitudinal axis 102 relative to the first coupling 200, the radial projections 232a travel in the slot(s) 322 of the second collar 320 along the acute angle defined by the slot(s) 322, which overcomes the latching force provided by the latch mechanism 258 and the latch engagement structure 338, and the causes the unlatching of the first valve 250 from the second valve 330.

When the latch mechanism 258 is engaged with the latch engagement structure 338, the face seal portion 264 of the first valve seal 260 resides between the front faces of the first valve 250 and the second valve 330. The engagement between the latch mechanism 258 and the latch engagement structure 338 ensures that there is a light longitudinal compression of the face seal portion 264 between the front faces of the first valve 250 and the second valve 330. Accordingly, no fluid can reside between the front faces of the first valve 250 and the second valve 330 as long as the first valve 250 and the second valve 330 are latched together via the latch mechanism 258 and the latch engagement structure 338.

In the depicted embodiment, the latch engagement structure 338 provides a radially outward extending protrusion that circumferentially surrounds the longitudinal axis 102 in a segmented manner. The latch mechanism 258 of the first valve 250 includes deflectable arms that define a corresponding segmented annular groove. When the first valve 250 and the second valve 330 longitudinally uncouple from each other, the deflectable arms of the latch mechanism 258 splay radially outward so that the circumferential protrusions of the latch engagement structure 338 can be removed from the annular groove of the latch mechanism 258.

The latch mechanism 258 and the latch engagement structure 338 are designed to allow relative rotation therebetween about the longitudinal axis 102. Such relative rotation between the latch mechanism 258 and the latch engagement structure 338 takes place during the second step of the disconnection process. During the second step of the disconnection process the first housing 210, the first termination and plunger member 220, and the first valve 250 are rotated relative to the second coupling 300 (including the second valve 330). That is, during the second step of the disconnection process the first valve 250 is rotated about the longitudinal axis 102 relative to the second valve 330.

Accordingly, the latch mechanism 258 and the latch engagement structure 338 also rotate about the longitudinal axis 102 relative to each other.

Figure 27:
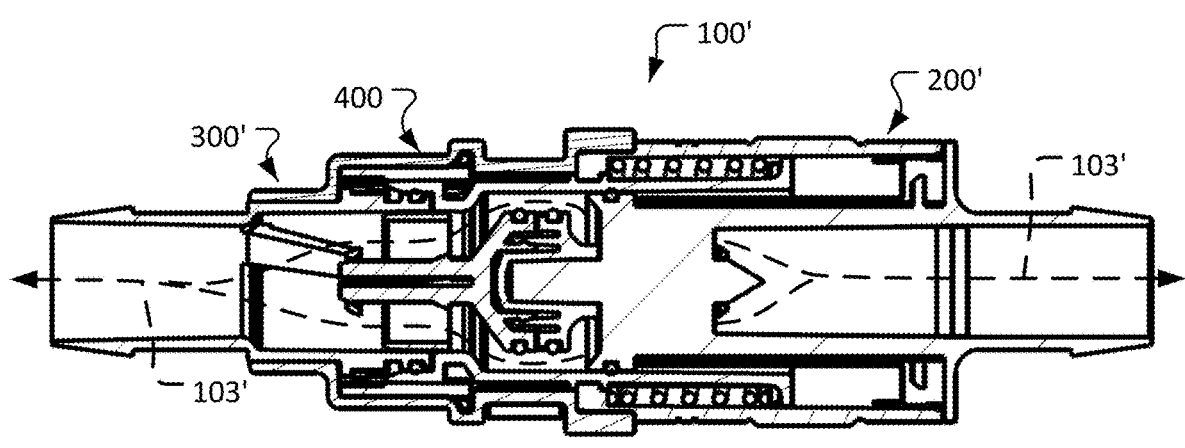
FIG. 27 is a longitudinal cross-sectional view of another example fluid coupling assembly in accordance with some embodiments.

FIG. 27 illustrates another example fluid coupling assembly 100'. The fluid coupling assembly 100' is functionally the same as the fluid coupling assembly 100 described above. The differences between the fluid coupling assembly 100' and the fluid coupling assembly 100 are that the valves and a couple of other components are different, as described further below. Components of the fluid coupling assembly 100' that are the same as those of the fluid coupling assembly 100 have the same reference numbers. Components of the fluid coupling assembly 100' that functionally similar to, but are designed differently than, those of fluid coupling assembly 100 have the same reference number with a prime symbol. For example, as shown in FIG. 27, the first fluid coupling 200' and the second fluid coupling 300' are functionally the same as the first fluid coupling 200 and the second fluid coupling 300 described above, but there are some design differences as described further below. In contrast, the removable sleeve 400 of the fluid coupling assembly 100' has the same function and is the same design as the removable sleeve 400 of the fluid coupling assembly 100 described above. Therefore, no prime symbol is added to its reference number.

The following description of the fluid coupling assembly 100' will focus on the aspects of the fluid coupling assembly 100' that are designed differently than those of the fluid coupling assembly 100. If no mention is made regarding particular aspects of the fluid coupling assembly 100' it is to be understood that those aspects are the same design as those of the fluid coupling assembly 100 described above.

In FIG. 27, the fluid coupling assembly 100' is shown in its operable configuration. Accordingly, an open fluid flow path 103' is defined through the first fluid coupling 200' and the second fluid coupling 300'. The fluid flow path 103' is different than the fluid flow path 103 of the fluid coupling assembly 100 because of the differences of the designs of certain components (e.g., the valves), as described further below. The fluid flow path 103' may have less flow resistance than the fluid flow path 103 of the fluid coupling assembly 100.

Figure 28:
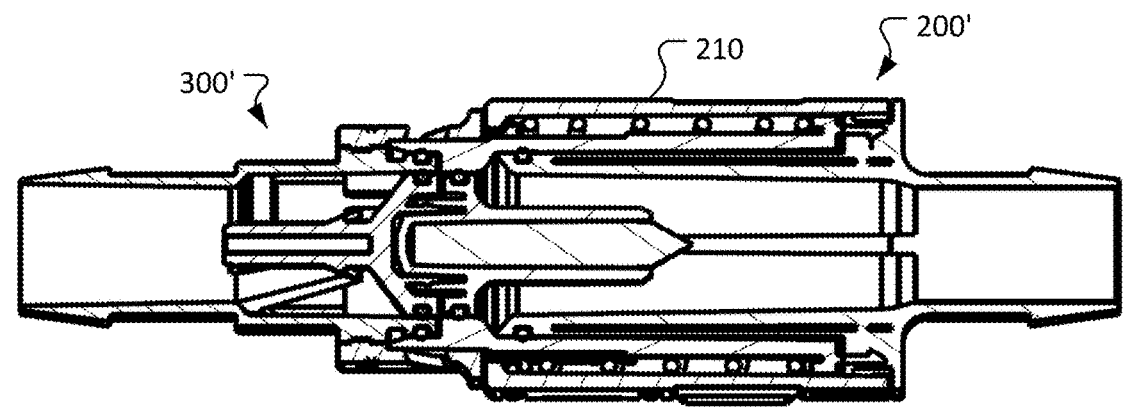
FIG. 28 shows the fluid coupling assembly of FIG. 27 in the process of being disconnected.
Figure 29:
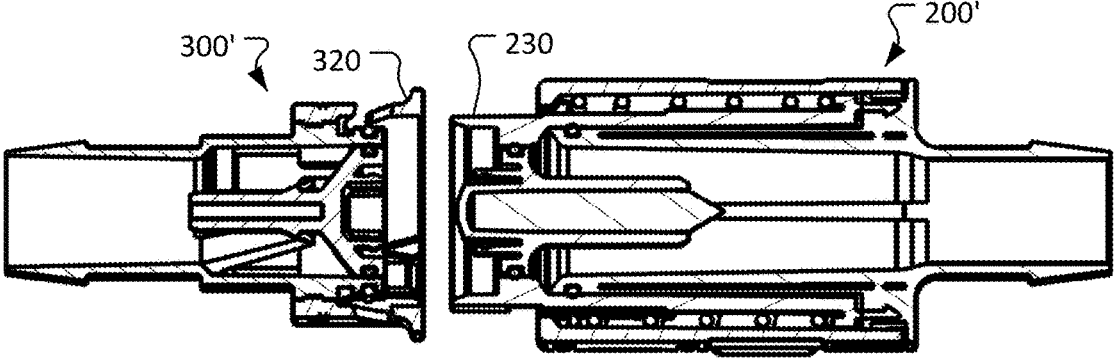
FIG. 29 shows the fluid coupling assembly of FIG. 27 after disconnection.

FIGS. 28 and 29 illustrate the process of disconnection of the fluid coupling assembly 100' (i.e., the disconnection of the first fluid coupling 200' from the second fluid coupling 300'). The process of disconnection of the fluid coupling assembly 100' is the same as the four-step disconnection process described above in reference to fluid coupling assembly 100. Accordingly, the fluid coupling assembly 100' provides an aseptic and non-spill disconnection functionality.

Figure 30:
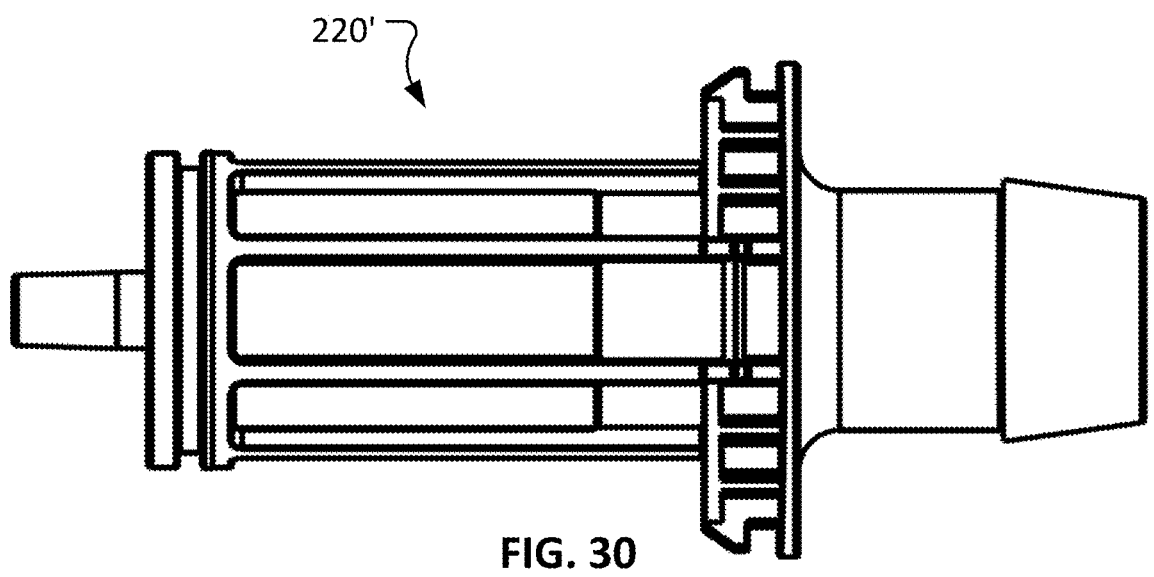
FIG. 30 is a side view of a termination and plunger member of a first coupling of the fluid coupling assembly of FIG. 27.
Figure 31:
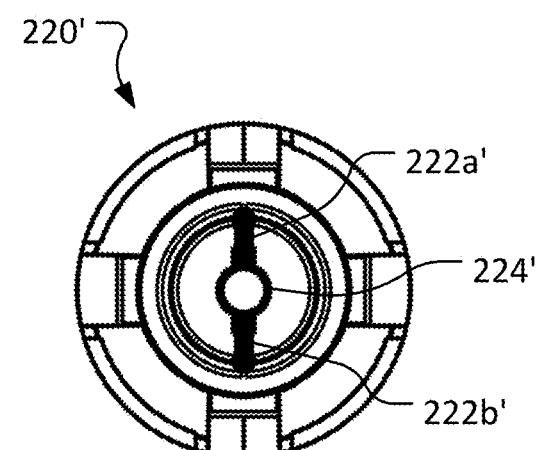
FIG. 31 is an end view of the termination and plunger member of FIG. 30.
Figure 32:
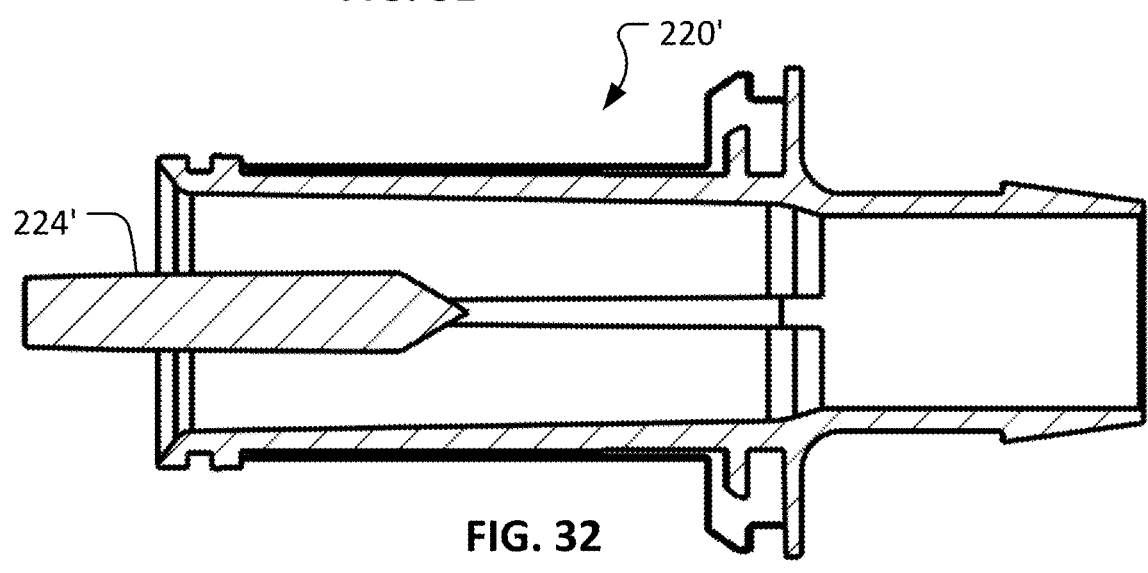
FIG. 32 is a longitudinal cross-sectional view of the termination and plunger member of FIG. 30.

FIGS. 30-32 illustrate the first termination and plunger member 220' of the first coupling 200'. The first valve 250' (as described below) and the first housing 210 (as described above) are fixedly coupled to the first termination and plunger member 220', and the three components function unitarily as a single component.

The first termination and plunger member 220' includes one or more ribs (two ribs 222a' and 222b' in the depicted embodiment) that extend radially inward from the inner wall of the first termination and plunger member 220' and that are fixedly coupled to a centrally located valve-mounting member 224'. The first valve 250' of the first coupling 200' is fixedly coupled to the valve-mounting member 224', as described further below.

Figure 33:
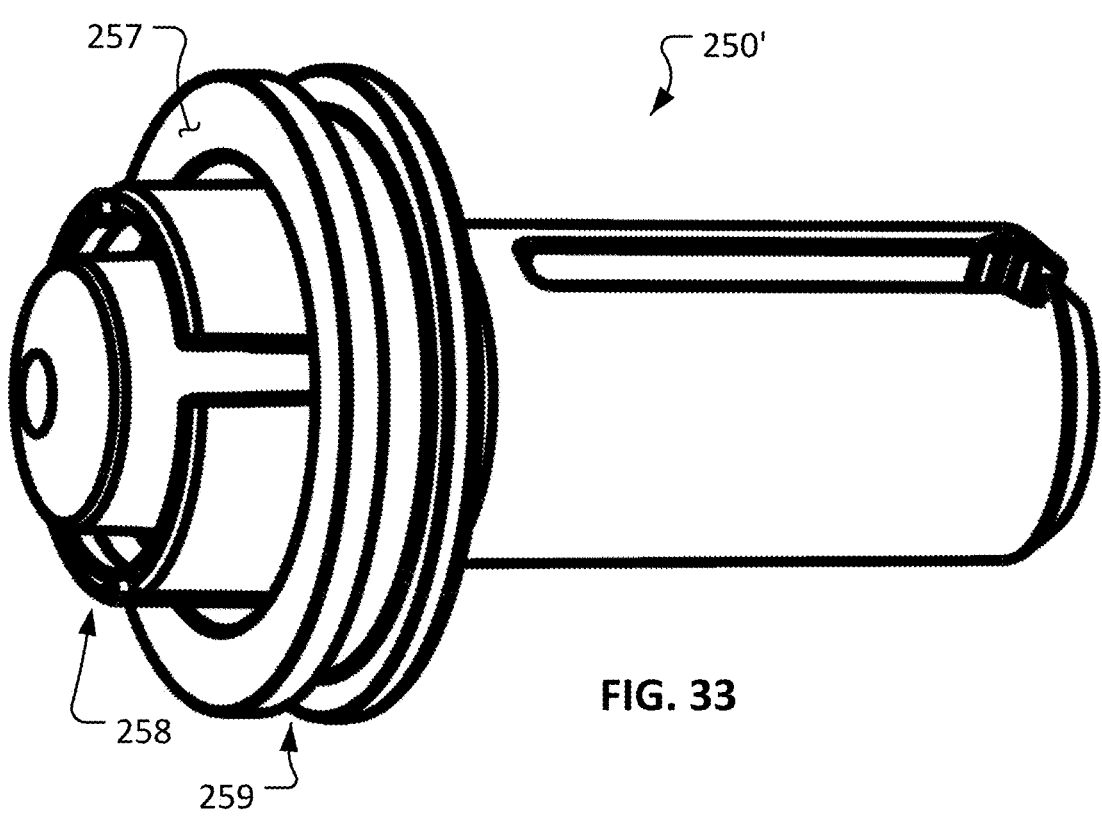
FIG. 33 is a perspective view of a first valve of a first coupling of the fluid coupling assembly of FIG. 27.
Figure 34:
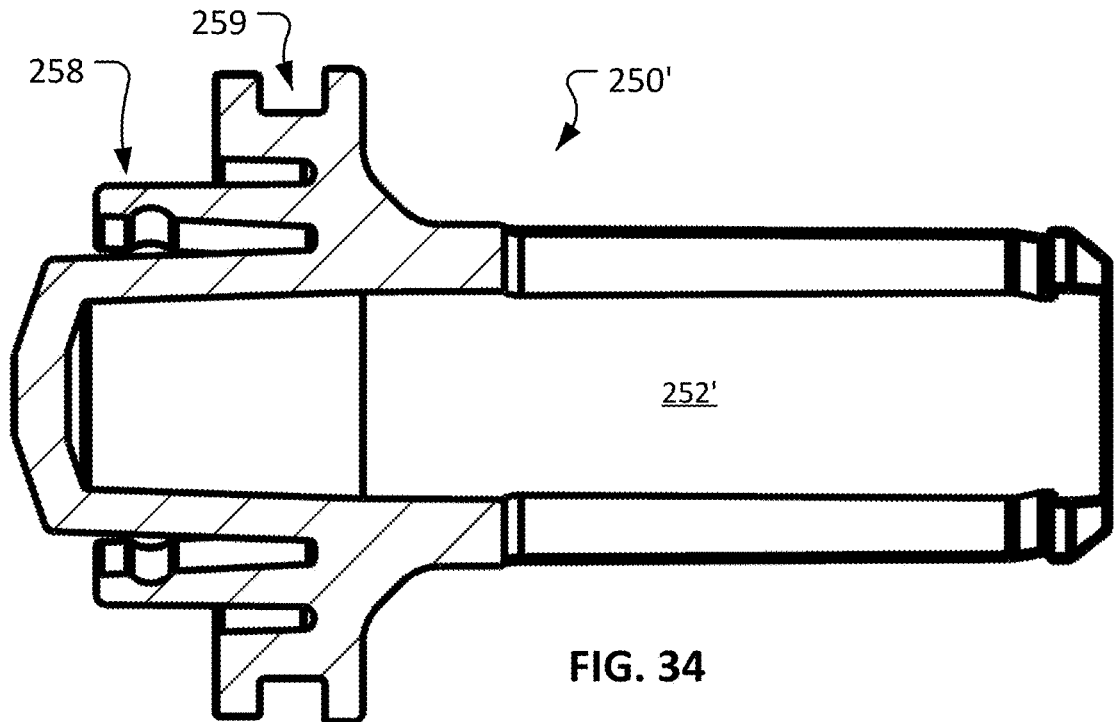
FIG. 34 is a longitudinal cross-sectional view of the first valve of FIG. 33.

FIGS. 33 and 34 illustrate the first valve 250' of the first coupling 200'. The first valve 250' defines an interior space 252' that receives the valve-mounting member 224' of the plunger member 220'. In some embodiments, the first valve 250' can snap into engagement with the valve-mounting member 224' when the valve-mounting member 224' is received in the interior space 252' of the first valve 250'.

Figures 35, 36, 37:
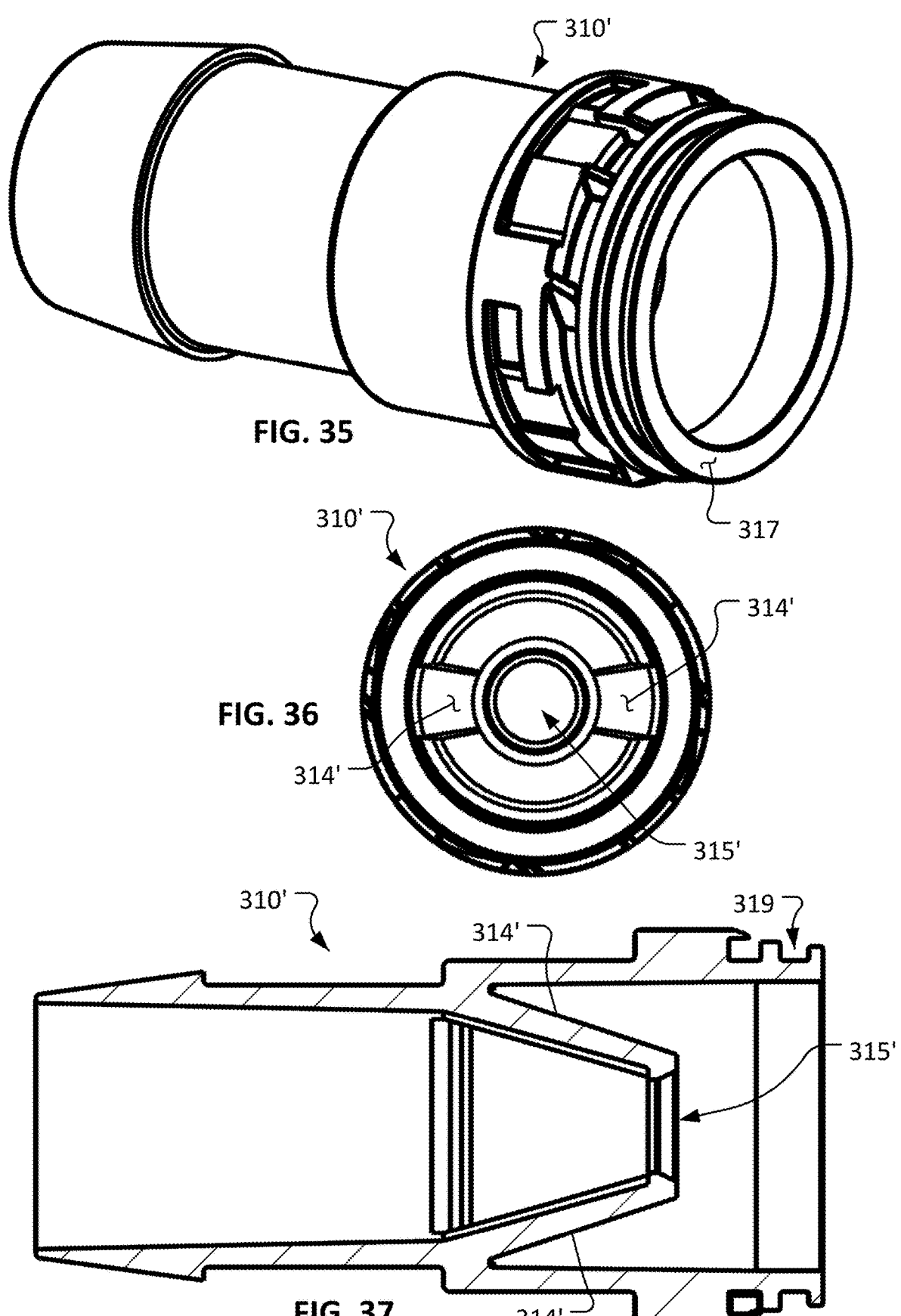
FIG. 35 is a perspective view of a second termination member of a second coupling of the fluid coupling assembly of FIG. 27.
FIG. 36 is an end view of the second termination member of FIG. 35.
FIG. 37 is a longitudinal cross-sectional view of the second termination member of FIG. 35.

FIGS. 35-37 illustrate the second termination member 310' of the second coupling 300'. The second termination member 310' includes one or more standoffs (two standoffs 314' in the depicted embodiment) that extend radially inward from the inner wall of the second termination member 310' and that define a central opening 315'. A portion of the second valve 330' is movably received in the central opening 315'.

Figure 38:
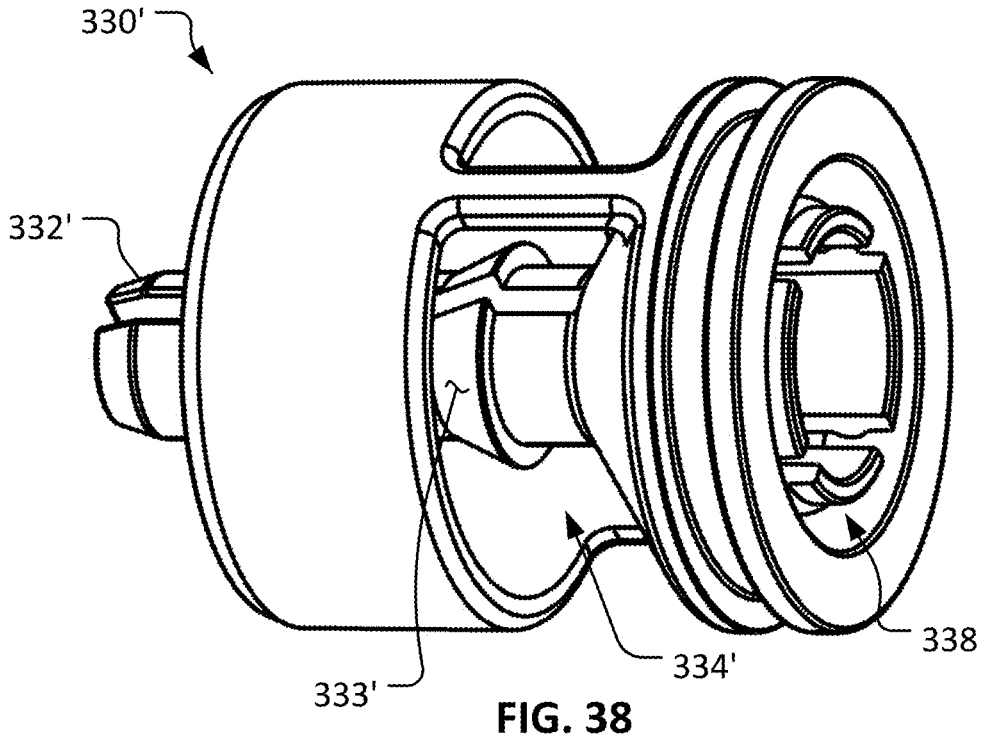
FIG. 38 is a perspective view of a second valve of a second coupling of the fluid coupling assembly of FIG. 27.
Figure 39:
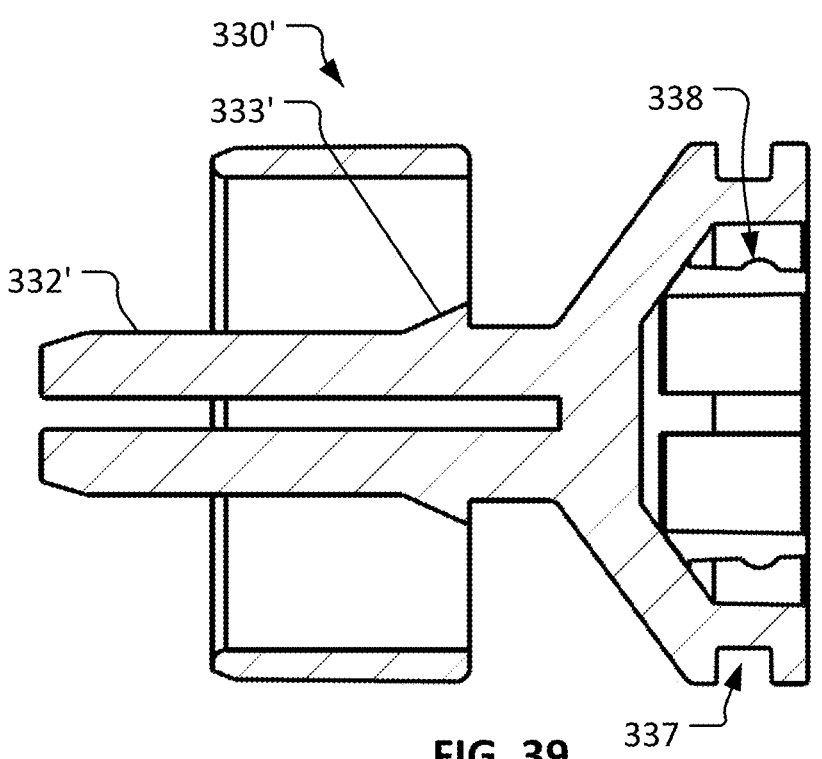
FIG. 39 is a longitudinal cross-sectional view of the second valve of FIG. 38.

FIGS. 38 and 39 illustrate the second valve 330' of the second coupling 300'. The second valve 330' includes a central shaft 332' that is movably received in the central opening 315'. Accordingly, second valve 330' is movable in relation to the second termination member 310' between a first extended configuration (e.g., as shown in FIG. 27) and a second retracted configuration (e.g., as shown in FIGS. 28 and 29). The second valve 330' translates along the longitudinal axis 102 as it reconfigures from its first extended configuration to its second retracted configuration. When the second valve 330' is in its second retracted configuration, two barbs 333' that radially extend from the central shaft 332' pass through the central opening 315' of the second termination member 310' in order to lock the second valve 330' is in its second retracted configuration. In the depicted embodiment, the central shaft 332' is longitudinally split to allow the two barbs 333' to pass through the central opening 315' of the second termination member 310'.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system modules and components in the embodiments described herein should not be understood as requiring such separation in all embodiments.

What is claimed is:

1. A single-use aseptic fluid coupling assembly defining a longitudinal axis and an open fluid flow path through the fluid coupling assembly along the longitudinal axis, the fluid coupling assembly comprising: a first coupling releasably connected to a second coupling, the first coupling comprising:
a first housing;
a first valve comprising a front face surface;

a first sleeve disposed between the first housing and the first valve, the first sleeve being translatable along the longitudinal axis; and
a first valve seal coupled to the first valve and covering at least a portion of the front face surface of the first valve;

the second coupling comprising:
a second coupling seal comprising: (i) a face seal pressing against the first sleeve and (ii) a circumferential radial seal pressing against the first sleeve; and
a second valve that is translatable along the longitudinal axis, the second valve comprising a front face surface, wherein the first valve seal is compressed between the front face surfaces of the first valve and the second valve.

2. The fluid coupling assembly of claim 1, wherein the first coupling further comprises:
a spring disposed between the first housing and the first sleeve.

3. The fluid coupling assembly of claim 2, wherein the spring is not in the open fluid flow path.

4. The fluid coupling assembly of claim 2, wherein the second coupling further comprises a collar, wherein the first sleeve is removably coupled to the collar, and wherein the first housing is spaced apart from the collar.

5. The fluid coupling assembly of claim 4, wherein the first sleeve includes one or more projections that are movably disposed in one or more slots defined by the collar.

6. The fluid coupling assembly of claim 5, wherein the one or more slots each include: (i) a circumferentially extending portion, (ii) a portion that extends along an acute angle relative to the longitudinal axis, and (iii) a longitudinally extending portion that has an open end.

7. The fluid coupling assembly of claim 6, wherein each projection of the one or more projections is movably disposed in the circumferentially extending portion of a slot of the one or more slots.

8. The fluid coupling assembly of claim 1, wherein the first valve defines an annular seal groove.

9. The fluid coupling assembly of claim 8, wherein the first valve seal includes an annular seal portion that is disposed within the annular seal groove of the first valve.

10. The fluid coupling assembly of claim 9, wherein the first valve includes a latch mechanism and the second valve includes a latch engagement structure that is releasably coupled with the latch mechanism, and wherein the latch mechanism extends through an opening defined by the first valve seal.

11. A single-use aseptic fluid coupling assembly comprising a first coupling connected to a second coupling, the fluid coupling assembly defining a longitudinal axis and an open fluid flow path through the fluid coupling assembly along the longitudinal axis, wherein the first coupling and second coupling are configured to be disconnected from each other by performing steps a-c:
(a) rotating a housing of the first coupling in a first direction about the longitudinal axis;
(b) translating the housing of the first coupling along the longitudinal axis toward the second coupling; and
(c) rotating the first coupling relative to the second coupling in a second direction about the longitudinal axis, wherein a first valve of the first coupling unlatches from a second valve of the second coupling during step (c).

12. The fluid coupling assembly of claim 11, wherein the first direction is opposite of the second direction.

13. The fluid coupling assembly of claim 11, wherein the fluid coupling assembly further comprises a removable sleeve surrounding portions of the first and second couplings.

14. The fluid coupling assembly of claim 13, wherein the removable sleeve must be uncoupled from the first and second couplings prior to performance of step (a).

15. The fluid coupling assembly of claim 11, wherein during the step (a) the housing is rotated about a sleeve of the first coupling.

16. The fluid coupling assembly of claim 15, wherein during the step (b) the housing is translated along the sleeve.

17. The fluid coupling assembly of claim 11, wherein the fluid coupling assembly includes structures that prevent performance of the steps a-c out of the sequential order.

18. The fluid coupling assembly of claim 11, wherein the first and second valves are releasably latched to each other during steps (a) and (b).

19. The fluid coupling assembly of claim 11, wherein the first valve of the first coupling and the second valve of the second coupling each move during the step (b) and close the open fluid flow path at the completion of the step (b).

20. The fluid coupling assembly of claim 11, wherein the fluid coupling assembly includes structures that prevent each of the steps a-c from being reversed after completion.

* * * * *